United States Patent [19]

Marcade et al.

[11] Patent Number: 5,993,481
[45] Date of Patent: Nov. 30, 1999

[54] MODULAR BIFURCATED INTRALUMINAL GRAFTS AND METHODS FOR DELIVERING AND ASSEMBLING SAME

[75] Inventors: Jean Paul Marcade, La Rochelle, France; Anthony West, Clearwater; Frederick W. Kornahrens, Palm Harbor, both of Fla.

[73] Assignee: InterVascular, Inc., Clearwater, Fla.

[21] Appl. No.: 08/840,406

[22] Filed: Apr. 29, 1997

Related U.S. Application Data

[62] Division of application No. 08/393,701, Feb. 24, 1995, Pat. No. 5,683,449.

[51] Int. Cl.$^6$ ........................................................ A61F 2/06
[52] U.S. Cl. .................................................. 623/1; 623/12
[58] Field of Search ........................... 623/1, 12; 606/198

[56] References Cited

U.S. PATENT DOCUMENTS

| | | | |
|---|---|---|---|
| 5,562,724 | 10/1996 | Vorwerk et al. | 623/1 |
| 5,575,817 | 11/1996 | Martin | 623/1 |
| 5,628,788 | 5/1997 | Pinchuk . | |
| 5,632,772 | 5/1997 | Alcime et al. . | |
| 5,639,278 | 6/1997 | Dereume et al. . | |
| 5,716,365 | 2/1998 | Goicoechea et al. . | |
| 5,723,004 | 3/1998 | Dereume et al. . | |

FOREIGN PATENT DOCUMENTS

| | | | |
|---|---|---|---|
| 2 678 508 A1 | 1/1993 | France | 623/1 |
| 9319267 U1 | 4/1994 | Germany | 623/1 |

OTHER PUBLICATIONS

Chuter, T., "Bifurcated Endovascular Graft Insertion for Abdominal Aortic Aneurysm," from Greenhalgh, *Vascular and Endovascular Surgical Techniques*, 3rd Edition, 1994, pp. 92–99.

Parodi, J.C., "Transfemoral Intraluminal Graft Implantation for Abdominal Aortic Aneurysms," from Greenhalgn, *Vascular and Endovascular Surgical Techniques*, 3rd Edition, 1994, pp. 71–77.

Moore, W.S., "Transfemoral Endovascular Repair of Abdominal Aortic Aneurysm Using the Endovascular Graft System Device," from Greenhalgh, *Vascular and Endovascular Surgical Techniques*, 3rd Edition, 1994, pp. 78–91.

Criado et al., "Transluminal Recanalization, Angioplasty and Stenting in Endovascular Surgery: Techniques and Applications," from Greenhalgh, *Vascular and Endovascular Surgical Techniques*, 3rd Edition, 1994, pp. 49–70.

Marin et al., "Endoluminal Stented Graft Aorto–Bifemoral Reconstruction," from Greenhalgh, *Vascular and Endovascular Surgical Techniques*, 3rd Edition, 1994, pp. 100–104.

May et al., "Transluminal Placement of a Prosthetic Graft-Stent Device for Treatment of Subclavian Artery Aneurysm," *Journal of Vascular Surgery*, vol. 18, No. 6, Dec. 1993, pp. 1056–1059.

Chuter et al., "Transfemoral Endovascular Aortic Graft Placement," *Journal of Vascular Surgery*, vol. 18, No. 2, Aug. 1993, pp. 185–197.

Parodi et al., "Transfemoral Intraluminal Graft Implantation for Abdominal Aortic Aneurysms," *Annals of Vascular Surgery*, vol. 5, No. 6, 1991, pp. 491–499.

*Primary Examiner*—David H. Willse
*Attorney, Agent, or Firm*—Lerner, David, Littenberg, Krumholz & Mentlik, LLP

[57] ABSTRACT

A bifurcated graft is formed from a series of individual components which are intraluminally delivered apart from one another and then assembled to form a fully supported structure. The modular system includes a base member and one or more grafts connected thereto. The base member preferably includes a portion which gradually increases in diameter. A tubular device for inserting the components of the modular system and a method employing the modular system for repairing an abdominal aortic aneurysm are also disclosed.

18 Claims, 11 Drawing Sheets

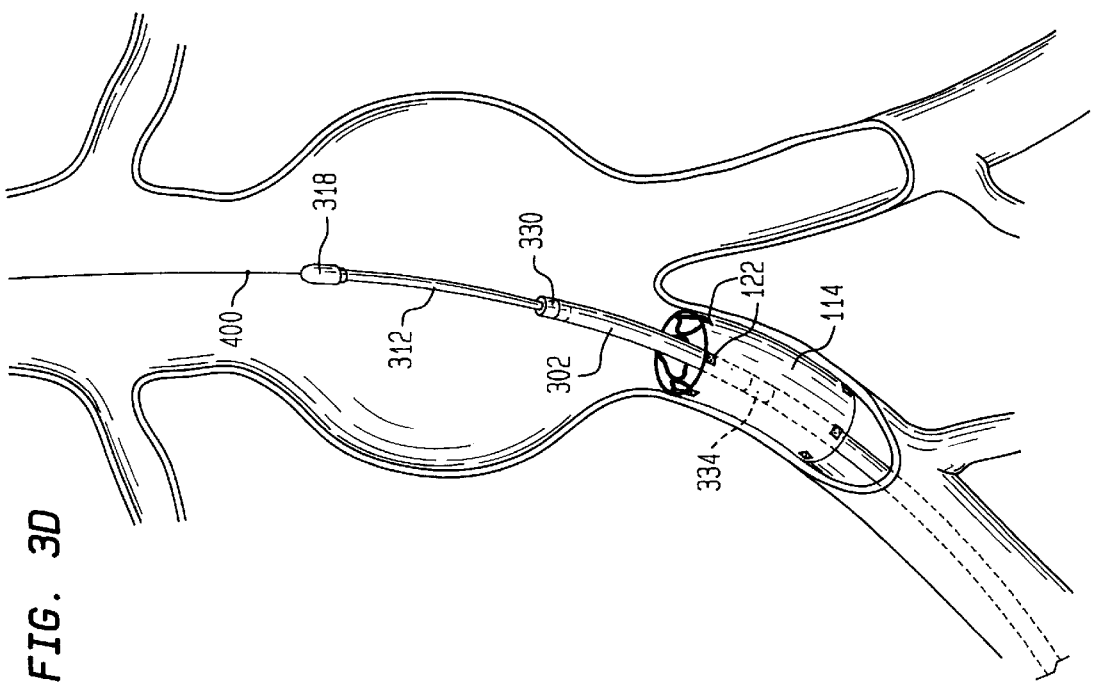
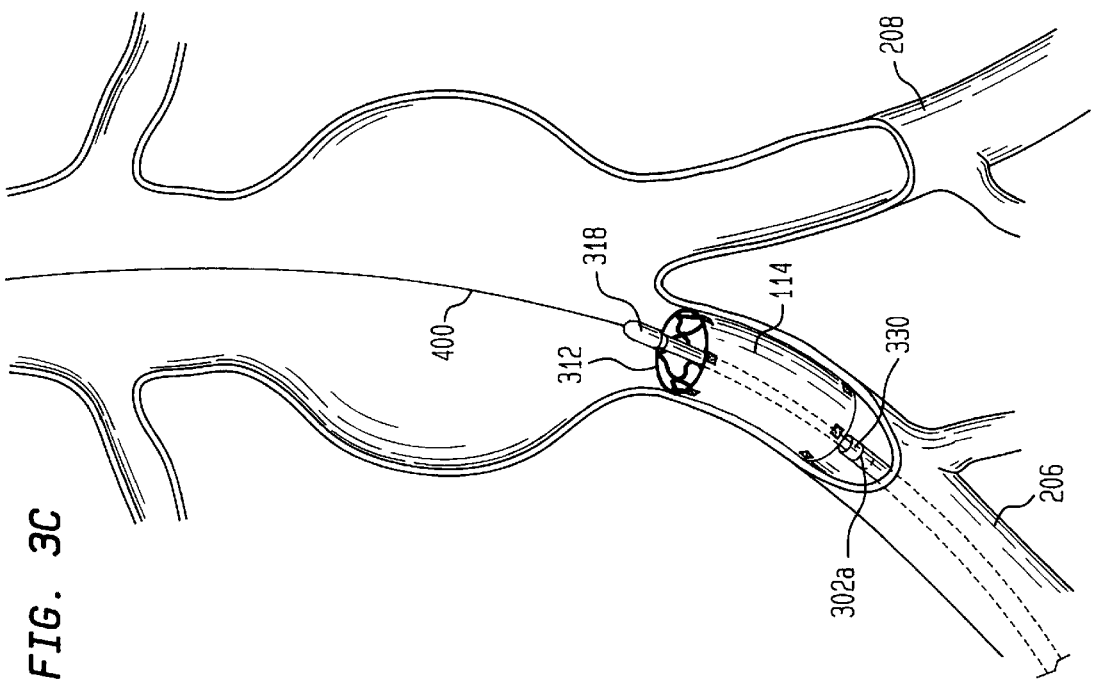
FIG. 3C
FIG. 3D

MODULAR BIFURCATED INTRALUMINAL GRAFTS AND METHODS FOR DELIVERING AND ASSEMBLING SAME

This is a division, of application Ser. No. 08/393,701 filed Feb. 24, 1995, now U.S. Pat. No. 5,683,449.

FIELD OF THE INVENTION

The present invention relates to bifurcated intraluminal grafts, particularly for repairing defects in arteries and other lumens within the body. More particularly, the present invention relates to modular systems for forming bifurcated grafts and to methods for delivering and assembling same in situ for repairing defective body lumens, and particularly abdominal aortic aneurysms.

BACKGROUND OF THE INVENTION

An abdominal aortic aneurysm is a sac caused by an abnormal dilation of the wall of the aorta as it passes through the abdomen. The aorta is the main artery of the body, supplying blood to all organs and parts of the body except the lungs. It arises from the left ventricle of the heart, passes upward, bends over and passes down through the thorax and through the abdomen, and finally divides into the two iliac arteries which supply blood to the pelvis and lower extremities.

The aneurysm ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is removed and replaced with a prosthetic device, such as a synthetic graft.

As with all major surgeries, there are many disadvantages to the foregoing surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the loss of the existing thrombosis to support and reinforce the graft; the unsuitability of the surgery for many patients, particularly older patients exhibiting co-morbid conditions; and the problems associated with performing the surgical procedure on an emergency basis after the aneurysm has already ruptured.

In view of the foregoing disadvantages of conventional surgical repair techniques, techniques have been developed for repairing abdominal aortic aneurysms by intraluminally delivering an aortic graft to the aneurysm site through the use of a catheter based delivery system, and securing the graft within the aorta using an expandable stent. Since the first documented clinical application of this technique was reported by Parodi et al. in the Annals of Vascular Surgery, volume 5, pages 491–499 (1991), the technique has gained more widespread recognition and is being used more commonly. As vascular surgeons have become more experienced with this endovascular technique, however, certain problems have been encountered. One problem has been the difficult nature of the procedure. Particularly complex is the step of transferring one leg of the graft from one iliac artery to the other, which requires the careful manipulation of numerous catheters and guide wires. Another problem has been the kinking and/or twisting of the graft both during and after the graft has been implanted. Still other problems relate to the need for accurate preoperative measurements to be made on the morphology of the aneurysm and the surrounding arterial structure, including the length of the aneurysm, the infrarenal aortic length and diameter, the length and diameter of the aorta between the aneurysm and the iliacs, the diameter of the iliacs, and the angle between the iliacs and the aorta. The difficulty in making these measurements accurately and the wide variations in these measurements among patients mandates that the bifurcated grafts be available in a wide range of sizes and configurations.

There therefore exists a need for a bifurcated graft and an implantation method which will overcome the foregoing deficiencies of the prior art. More particularly, there exists a need for a modular graft system which will more accurately accommodate the widely varying arterial sizes in patients, as well as the other size considerations faced by the surgeon. There also exists a need for a method for delivering and implanting a bifurcated graft which avoids the complex procedure for implanting prior art bifurcated grafts.

SUMMARY OF THE INVENTION

The present invention addresses the needs.

One aspect of the present invention provides a modular prosthesis for repairing a tubular anatomical structure consisting of a base member foldable radially between a collapsed configuration and an expanded configuration and extending longitudinally between a proximal end and a distal end, a primary tubular limb foldable radially between a collapsed configuration and an expanded configuration and having a proximal end and a distal end, and joining means for intraluminally joining the distal end of the primary limb to the proximal end of the base member. Preferably, the joining means includes a friction fit engagement between the distal end of the primary limb in the expanded configuration and the proximal end of the base member in the expanded configuration.

In accordance with one embodiment of the modular prosthesis, the primary limb may have a first diameter at its proximal end and a second diameter less that the first diameter at its distal end. In this regard, the diameter of the primary limb may decrease from the proximal end toward the distal end at an angle of taper between about 2 degrees and about 15 degrees. In preferred embodiments, the primary limb may have a diameter at its proximal end of between about 16 mm and about 36 mm in the expanded configuration and a diameter at its distal end of between about 16 mm and about 25 mm in the expanded configuration. The primary limb may also have a length from its proximal end to its distal end of between about 6 cm and about 15 cm. Desirably, the primary limb includes an annular sleeve at its distal end, the annular sleeve having a substantially uniform diameter. The primary limb may also include securing means at its proximal end for securing the primary limb to the tubular anatomical structure.

The base member may have a first diameter at its proximal end and a second diameter greater than the first diameter at its distal end. In preferred embodiments, the base member may have a diameter at its proximal end of between about 16 mm and about 25 mm in the expanded configuration. The base member may also include an annular sleeve at its proximal end, the annular sleeve having a substantially uniform diameter. Preferably, the annular sleeve has a length between about 2 cm and about 15 cm.

The base member and the primary limb may both consist of a flexible layer which is radially supported along substantially its entire length by an expandable stent. In one embodiment, the expandable stent may be formed from a high shape-memory material. In another embodiment, the expandable stent may be formed from a low shape-memory material.

In accordance with another embodiment hereof, the base member may include dividing means for forming first and second passageways communicating between the proximal and distal ends of the base member. The dividing means may include a line of stitching joining one surface of the base member to an opposite surface of the base member. Alternatively, the dividing means may include a web of material arranged longitudinally inside the base member and defining a first substantially round aperture adjacent the distal end of the base member and a second substantially round aperture at a spaced distance from the distal end of the base member. Preferred embodiments may further include at least one secondary tubular limb foldable radially between a collapsed configuration and an expanded configuration and having a proximal end and a distal end, and connecting means for connecting the proximal end of the secondary limb to the distal end of the base member.

In accordance with a further embodiment of the present invention, a modular prosthesis for repairing a tubular anatomical structure consists of a base member foldable radially between a collapsed configuration and an expanded configuration and having a proximal end and a distal end, a primary tubular limb foldable radially between a collapsed configuration and an expanded configuration and having a proximal end and a distal end, joining means for intraluminally joining the distal end of the primary limb to the proximal end of the base member, at least one secondary tubular limb foldable radially between a collapsed configuration and an expanded configuration and having a proximal end and a distal end, and connecting means for connecting the proximal end of the secondary limb to the distal end of the base member. The secondary limb may have a substantially uniform diameter of between about 10 mm and about 25 mm in the expanded configuration. Alternatively, the proximal end of the secondary limb may have a diameter which is different than the diameter on its distal end. Preferably, the secondary limb has a length between its proximal end and its distal end of between about 4 cm and about 15 cm.

In this last embodiment, the base member may include a main leg on its proximal end and first and second legs on its distal end. The main leg may extend in an axial direction and have a main passageway extending longitudinally therein and defining an inlet on its free end. The first leg may be oriented at a first angle to the axial direction and have a passageway extending longitudinally therein and communicating with the main passageway, and may define a first outlet on its free end. The second leg may be oriented at a second angle to the axial direction and have a passageway extending longitudinally therein and communicating with the main passageway, and the second leg may define a second outlet on its free end. The first angle may be different than the second angle, but each of the first and second angles are preferably between about 10 degrees and about 60 degrees. Also, the main leg may be oriented in a primary plane, and at least one of the first and second legs may be oriented in a plane different than the primary plane.

In a variant of this last embodiment, the base member may include a crotch defined between the first and second legs, the first leg having a length between the crotch and the first outlet of between about 2 cm and about 15 cm. Preferably, the first leg has a substantially uniform diameter of between about 10 mm and about 25 mm in the expanded configuration, and the second leg has a diameter which decreases in size from the second outlet toward the main leg.

This last embodiment may further include another secondary tubular limb foldable radially between a collapsed configuration and an expanded configuration and having a proximal end and a distal end, and attaching means for attaching the proximal end of the another secondary limb to the distal end of the base member. The another secondary limb may have a length between its proximal end and its distal end of between about 4 cm and about 15 cm, and a substantially uniform diameter of between about 10 mm and about 25 mm in the expanded configuration. Alternatively, the another secondary limb may have a first diameter at its proximal end and a second diameter at its distal end different than the first diameter.

In yet another embodiment of the present invention, a modular prosthesis for repairing a tubular anatomical structure may consist of a base member extending longitudinally between a proximal end defining an inlet and a distal end defining first and second outlets, the base member being foldable radially between a collapsed configuration and an expanded configuration, and a primary tubular limb having a proximal end and a distal end and being foldable radially between a collapsed configuration and an expanded configuration. The distal end of the primary limb in the expanded configuration may be matable in overlapping circumferential engagement with the inlet of the base member when the base member is in the expanded configuration to join the primary limb to the base member. The modular prosthesis may also include at least one secondary tubular limb having a proximal end and a distal end and being foldable radially between a collapsed configuration and an expanded configuration. The proximal end of the at least one secondary limb may be matable in overlapping circumferential engagement with one of the first and second outlets of the base member when the base member is in the expanded configuration to join the at least one secondary limb to the base member. Another secondary tubular limb may also be provided in which its proximal end is matable in overlapping circumferential engagement with another of the first and second outlets of the base member when the base member is in the expanded configuration to join the another secondary limb to the base member.

Another aspect of the present invention provides a prosthesis for repairing a tubular anatomical structure consisting of a hollow tubular body constructed from a woven fabric and having a length defined between a first end and a second end, the first end having a first diameter and the second end having a second diameter, the body having a diameter intermediate the first and second ends which is less than at least one of the first and second diameters. The first diameter may also be less than the second diameter. The first end of the body may have a diameter between about 16 mm and about 25 mm and the second end of the body may have a diameter between about 16 mm and about 36 mm. The diameter of at least a portion of the body may increase in size at an angle of taper between about 2 degrees and about 15 degrees, preferably at an angle of taper of about 4 degrees. The body may also have a length between about 6 cm and about 15 cm. Preferably, the body also includes an annular sleeve integrally formed at one end, the annular sleeve having a substantially uniform diameter.

Preferred embodiments of this aspect of the present invention may further include an expandable stent assembled to the body and radially supporting the body along substantially the entirety of its length. The expandable stent may be assembled in the interior of the body or on the exterior of the body, and may be formed from a high shape-memory material or from a low shape-memory material.

Yet another aspect of the present invention provides a method for repairing a tubular anatomical structure having a proximal branch and a pair of distal branches projecting from the proximal branch at a point of bifurcation. A method in accordance with this aspect of the present invention may include the steps of providing a first tubular limb foldable radially between a collapsed configuration and an expanded configuration and having a proximal end and a distal end, providing a base member foldable radially between a collapsed configuration and an expanded configuration and having an inlet and first and second outlets, and providing a primary tubular limb foldable radially between a collapsed configuration and an expanded configuration and having a proximal end and a distal end. The first limb may be fed in the collapsed configuration through one distal branch until its proximal end is positioned adjacent the point of bifurcation and its distal end is positioned within the one distal branch. The first limb may then be expanded from the collapsed configuration to the expanded configuration whereupon it engages and becomes secured within the one distal branch.

The base member may then be fed in the collapsed configuration through the one distal branch and the first limb until the inlet is positioned in the proximal branch, the first outlet is positioned within the proximal end of the first limb, and the second outlet is at least partially aligned with the other distal branch. The base member may then be expanded from the collapsed configuration to the expanded configuration, whereupon the first outlet engages the proximal end of the first limb in friction fit circumferential contact to join the first outlet of the base member to the first limb.

The primary limb may be fed in the collapsed configuration through one of the distal branches and one of the first and second outlets of the base member until its proximal end is positioned in the proximal branch and its distal end is positioned within the inlet of the base member. The primary limb may then be expanded from the collapsed configuration to the expanded configuration, whereupon its distal end engages the inlet in friction fit circumferential contact to join the primary limb to the inlet of the base member and its proximal end engages and becomes secured within the proximal branch.

Preferred methods may further include the steps of providing a second tubular limb foldable radially between a collapsed configuration and an expanded configuration and having a proximal end and a distal end, feeding the second limb in the collapsed configuration through the other distal branch until its proximal end is positioned within the second outlet of the base member and its distal end is positioned within the other distal branch, and expanding the second limb from the collapsed configuration to the expanded configuration, whereupon its proximal end engages the second outlet of the base member in friction fit circumferential contact to join the second limb to the second outlet of the base member and its distal end engages and becomes secured within the other distal branch. The steps of feeding and expanding the second limb may occur prior to the steps of feeding and expanding the primary limb.

Another method in accordance with the present invention may include the steps of providing a base member foldable radially between a collapsed configuration and an expanded configuration and having an inlet and first and second outlets, and providing a primary tubular limb foldable radially between a collapsed configuration and an expanded configuration and having a proximal end and a distal end. The base member may be fed in the collapsed configuration through one of the distal branches until the inlet is positioned in the proximal branch, the first outlet is positioned within the one distal branch, and the second outlet is at least partially aligned with the other distal branch, and expanded from the collapsed configuration to the expanded configuration, whereupon the first outlet engages and becomes secured within the one distal branch. The primary limb may be fed in the collapsed configuration through one of the distal branches and one of the first and second outlets of the base member until its proximal end is positioned in the proximal branch and its distal end is positioned within the inlet of the base member. The primary limb may be expanded from the collapsed configuration to the expanded configuration, whereupon its distal end engages the inlet in friction fit circumferential contact to join the primary limb to the base member and its proximal end engages and becomes secured within the proximal branch.

This last method may further include the steps of providing a first tubular limb foldable radially between a collapsed configuration and an expanded configuration and having a proximal end and a distal end, feeding the first limb in the collapsed configuration through the other distal branch until its proximal end is positioned within the second outlet of the base member and its distal end is positioned within the other distal branch, and expanding the first limb from the collapsed configuration to the expanded configuration, whereupon its proximal end engages the second outlet of the base member in friction fit circumferential contact to join the first limb to the second outlet of the base member and its distal end engages and becomes secured within the other distal branch.

A still further method for repairing anatomical structures in accordance with the present invention may include the steps of providing a primary tubular limb foldable radially between a collapsed configuration and an expanded configuration and having a proximal end and a distal end, and providing a base member foldable radially between a collapsed configuration and an expanded configuration and having a proximal end and a distal end. The primary limb may be fed in the collapsed configuration through one distal branch until it is positioned entirely in the proximal branch, and expanded from the collapsed configuration to the expanded configuration, whereupon it engages and becomes secured within the proximal branch. The base member may be fed in the collapsed configuration through one distal branch until its proximal end is positioned within the distal end of the primary limb, and expanded from the collapsed configuration to the expanded configuration, whereupon its proximal end engages the distal end of the primary limb in friction fit circumferential contact to join the base member to the primary limb. In preferred methods, the step of feeding the base member may include the step of positioning the base member so that its distal end rests upon the point of bifurcation when the base member is joined to the primary limb.

In a variant of this last method, the base member may include first and second passageways providing communication between its proximal and distal ends, and the method may include the further steps of providing a first tubular limb foldable radially between a collapsed configuration and an expanded configuration and having a proximal end and a distal end, feeding the first limb in the collapsed configuration through one distal branch until its proximal end is positioned within one passageway of the base member and its distal end is positioned within the one distal branch, and expanding the first limb from the collapsed configuration to the expanded configuration, whereupon its proximal end engages the one passageway of the base member in friction fit circumferential contact to join the first limb to the base member and its distal end engages and becomes secured within the one distal branch. The method may further include the steps of providing a second tubular limb foldable radially between a collapsed configuration and an expanded configuration and having a proximal end and a distal end, feeding the second limb in the collapsed configuration through the other distal branch until its proximal end is positioned within the other passageway of the base member and its distal end is positioned within the other distal branch, and expanding the second limb from the collapsed configuration to the expanded configuration, whereupon its proximal end engages the other passageway of the base member in friction fit circumferential contact to join the second limb to the base member and its distal end engages and becomes secured within the other distal branch.

Yet a further method for repairing a tubular anatomical structure in accordance with the present invention may include the steps of providing a component foldable radially between a collapsed configuration and an expanded configuration and having a proximal end with a first diameter, a distal end with a second diameter, and a diameter intermediate its proximal and distal ends which is less than at least one of the first and second diameters. The component may be fed in the collapsed configuration through one distal branch until it is positioned entirely in the proximal branch, and expanded from the collapsed configuration to the expanded configuration, whereupon the component engages and becomes secured within the proximal branch.

In this last method, the component may include first and second passageways providing communication between its proximal and distal ends, and the method may include the added steps of providing a first tubular limb foldable between a collapsed configuration and an expanded configuration and having a proximal end and a distal end, feeding the first limb in the collapsed configuration through one distal branch until its proximal end is positioned within one passageway of the component and its distal end is positioned within the one distal branch, and expanding the first limb from the collapsed configuration to the expanded configuration, whereupon its proximal end engages within the one passageway of the component in friction fit circumferential contact to join the first limb to the component and its distal end engages and becomes secured within the one distal branch. Preferred methods may further include the steps of providing a second tubular limb foldable radially between a collapsed configuration and an expanded configuration and having a proximal end and a distal end, feeding the second limb in the collapsed configuration through the other distal branch until its proximal end is positioned within the other passageway of the component and its distal end is positioned within the other distal branch, and expanding the second limb from the collapsed configuration to the expanded configuration, whereupon its proximal end engages within the other passageway of the component in friction fit circumferential contact to join the second limb to the component and its distal end engages and becomes secured within the other distal branch.

The modular graft system and surgical methods of the present invention overcome many of the difficulties associated with delivering and securing the bifurcated grafts of the prior art. By providing a graft in the form of modular components that can be individually selected and assembled together, the present invention permits more accurate sizing of the graft to the individual patient. Moreover, the modular system forms grafts having a fully supported structure which is much stronger than the prior art grafts and which obviates the prior art procedures in which the graft is secured by hanging at the proximal neck of the aneurysm, which arrangement is prone to acute and chronic failure whereby the graft could become displaced or collapsed. The modular system of the present invention further takes advantage of the flow of blood through the individual components to lock the components to one another, thereby assuring a secure assembly and minimizing the possibility of leakage.

BRIEF DESCRIPTION OF THE DRAWINGS

A more complete appreciation of the subject matter of the present invention and the various advantages thereof can be realized by reference to the following detailed description, in which reference is made to the accompanying drawings in which:

FIGS. 3A–J are highly schematic partial cross-sectional views of an abdominal aortic aneurysm showing the sequence of steps to repair same using the modular system shown in FIG. 1;

FIG. 9 is a perspective view of a delivery catheter assembly for use in connection with the modular system shown in.. FIG. 1, the sheath of the delivery catheter assembly being in the fully retracted position and being partially broken away to show the interior thereof.

DETAILED DESCRIPTION OF THE PREFERRED EMBODIMENTS

Figure 1:
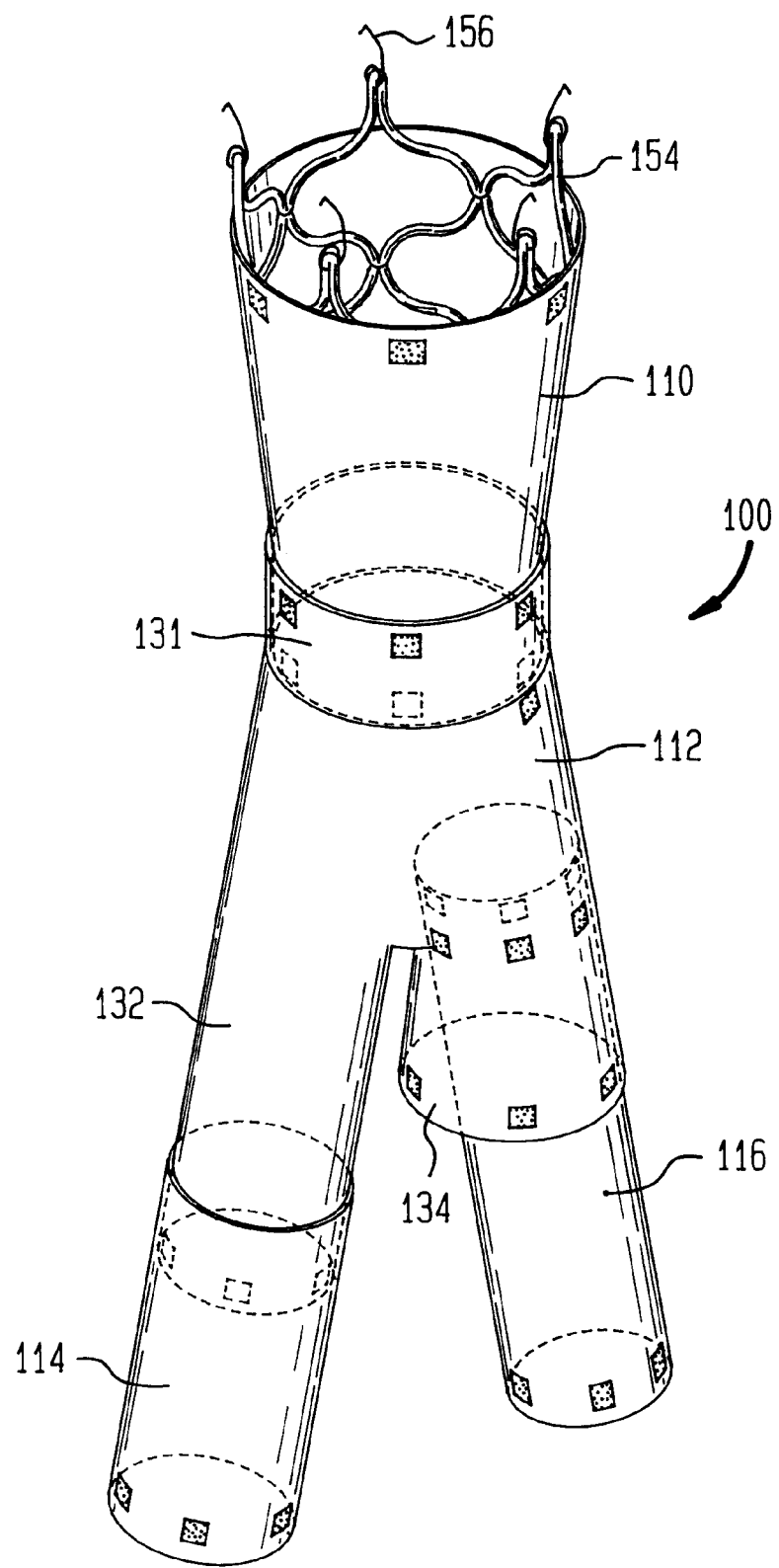
FIG. 1 is a perspective assembled view of a modular system for forming a bifurcated graft in accordance with one embodiment of the present invention.

In the detailed description which follows, the features of the present invention will be described in connection with the repair of an abdominal aortic aneurysm. A typical abdominal aortic aneurysm is illustrated in FIGS. 3A–J, in which the wall of the aorta 200 is weakened and forms a bulge 202 in the region between the renal arteries 204 and the point at which the aorta 200 branches into the right iliac artery 206 and left iliac artery 208. It will be appreciated, however, that the various features of the present invention may be readily utilized to repair defects in any body lumen which branches into two or more lumens. Indeed, the features of the present invention may be utilized to repair a variety of defects in a body lumen even where the lumen does not have branches associated with it.

Figure 2:
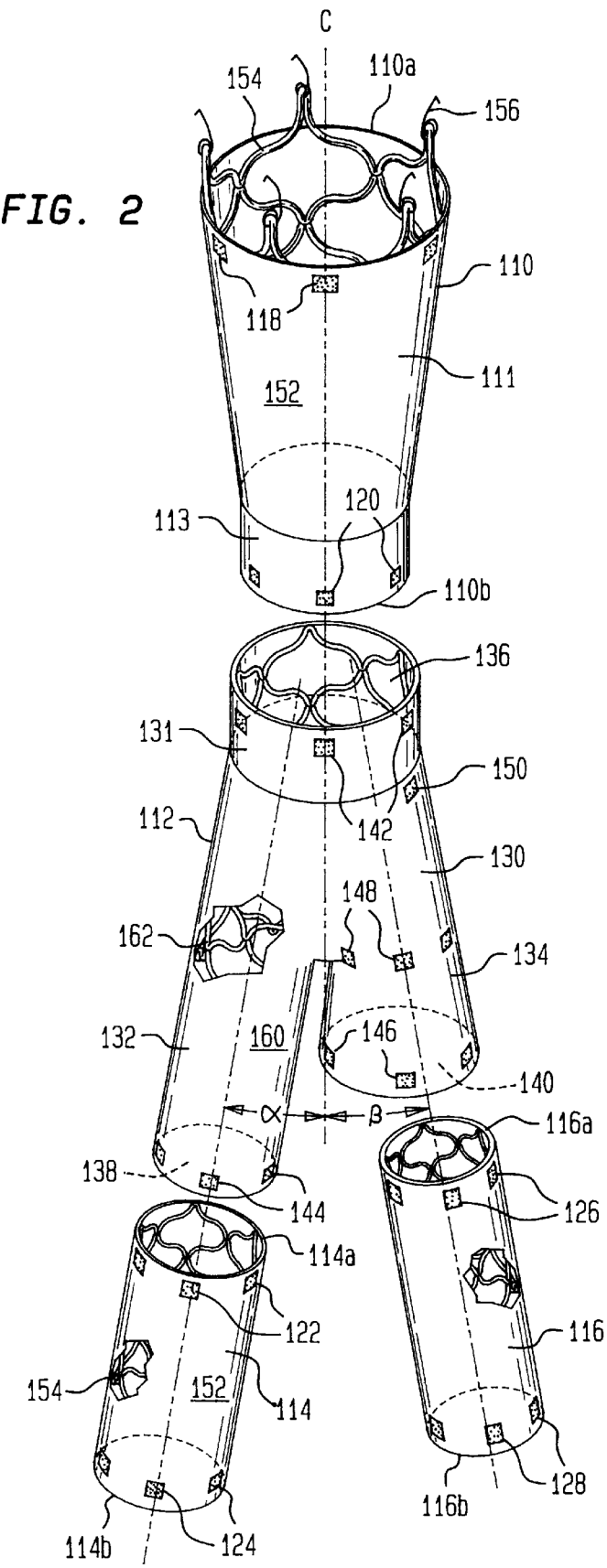
FIG. 2 is an exploded, perspective view of the modular system of FIG. 1, partially broken away to reveal the stent structures in the interior thereof.

Referring to FIGS. 1 and 2, there is illustrated one preferred embodiment of a modular system 100 for forming a bifurcated graft in accordance with one aspect of the present invention. As used herein, the term "modular" refers to the fact that system 100 includes a number of individual components which may be separately delivered by intraluminal techniques to the aneurysm site and then interconnected with one another in situ to form the bifurcated graft. Each of the components of modular system 100 is a fully supported structure which provides sufficient strength to permit the in situ construction of the bifurcated graft. In accordance with one embodiment hereof, modular system 100 includes a primary graft 110, a base member 112, and first and second grafts 114 and 116, respectively, all of which are fabricated as separate components which may be assembled in preselected size combinations depending upon the arterial morphology presented by the patient. Accordingly, each of the various components is preferably provided in a range of sizes sufficient to accommodate the arterial morphology which the surgeon is likely to face in the vast majority of patients.

Primary graft 110 preferably includes a main tapered portion 111 and an annular sleeve 113 having a substantially uniform diameter, tapered portion 111 and sleeve 113 together defining the overall length of primary graft 110 between proximal end 110a and distal end 110b. As used herein, the term "proximal" refers to the end of a component which is upstream or closest to the heart, and the term "distal" refers to the end of a component which is downstream or farthest away from the heart. Primary graft 110 may be provided in a number of lengths ranging from about 6 cm to about 15 cm in increments of about 10 mm, and in a number of diameters in the expanded condition ranging from about 16 mm to about 36 mm at the proximal end 110a and from about 16 mm to about 25 mm at the distal end 110b, both in increments of about 2 mm. Preferably, graft 110 is provided in a range of lengths from about 8 cm to about 12 cm at about 10 mm increments, in a range of diameters at proximal end 110a from about 24 mm to about 36 mm in increments of about 2 mm in the expanded condition, and with a diameter of about 22 mm in the expanded condition at distal end 110b. Furthermore, graft 110 may take the form of a series of two or more grafts which are shorter in length than graft 110 but which can be assembled to one another in succession during the surgical procedure described below to form a primary graft having the desired length.

The tapered portion 111 of primary graft 110 preferably has an angle of taper between about 2 degrees and about 15 degrees from the centerline thereof, with an angle of taper of about 4 degrees being most preferred. It will be appreciated, of course, that the lengths and diameters of primary graft 110 may be provided in wider or more narrow increments depending upon the size variations in the aorta which surgeons experience from patient to patient. Furthermore, the foregoing dimensions are for use in repairing an abdominal aneurysm; the components of a modular system for repairing other body lumens thus may be provided in different size ranges and in different increments.

Primary graft 110 desirably includes a first series of radiomarkers 118 positioned around the periphery of proximal end 110a, and a second series of radiomarkers 120 positioned around the periphery of distal end 110b. Such radiomarkers are conventional in the art and, when viewed under fluoroscopy, enable the surgeon to identify and properly locate the ends of primary graft 110 during surgical implantation. Thus, radiomarkers 118 and 120 may be formed from biocompatible metals, such as, for example, stainless steel or platinum-iridium, which are radioopaque, or from radioopaque polymers.

Grafts 114 and 116 are similar in construction to primary graft 110. Thus, grafts 114 and 116 preferably have a generally cylindrical tubular construction with graft 114 having a proximal end 114a and a distal end 114b and graft 116 having a proximal end 116a and a distal end 116b. Grafts 114 and 116 may be provided in a number of lengths ranging from about 4 cm to about 15 cm in increments of about 10 mm, and in a number of diameters in the expanded condition ranging from about 10 mm to about 25 mm in increments of about 2 mm. Grafts 114 and 116 preferably are provided in lengths from about 4 cm to about 8 cm in 10 mm increments, and with diameters in 2 mm increments from about 12 mm to about 16 mm in the expanded configuration. In contrast to the tapered configuration of primary graft 110, grafts 114 and 116 may have a substantially uniform diameter along their entire lengths between the proximal and distal ends. However, it is contemplated that grafts 114 and 116 may have a tapered configuration similar to that of graft 110, wherein the diameter of the graft may either increase or decrease from the proximal to the distal end thereof. Such tapered grafts are particularly useful, for example, in those situations where the aneurysmal condition extends from the aorta into the iliac, enabling the graft to have a larger diameter where it will lie in the bulged portion of the iliac and a smaller diameter where it will lie in the normal portion of the iliac.

Grafts 114 and 116 also preferably include a series of radiomarkers at their respective ends. Thus, graft 114 may include a first series of radiomarkers 122 positioned along the periphery of proximal end 114a and a second series of radiomarkers 124 positioned along the periphery of distal end 114b. Similarly, graft 116 may include one series of radiomarkers 126 positioned along the periphery of proximal end 116a and another series of radiomarkers 128 positioned along the periphery of distal end 116b.

Base member 112 is a hollow generally Y-shaped structure formed by a frustoconical main body 130 which branches into two legs 132 and 134. Leg 132 may have a generally cylindrical shape with a substantially uniform diameter from its juncture with main body 130 to the free end thereof. Leg 134, on the other hand, defines a skirt which gradually increases in diameter from its juncture with main body 130 to its free end. Opposite legs 132 and 134, main body 130 may include an annular sleeve 131 having a substantially uniform diameter, the free end of which defines an inlet 136 on the proximal end of base member 112, while outlets 138 and 140 are defined at the free ends of legs 132 and 134, respectively. Base member 112 may be formed by the same methods, discussed in detail below, which are used to form the taper of primary graft 110. That is, a tapered tubular "blank" may initially be woven with an annular sleeve 131 formed on one end. Leg 132 may then be created by sewing upwardly from the enlarged end of the tapered portion and parallel to the wall thereof with an overlapping edge stitch. The stitch may then be continued to form the crotch area of base member 112 and then downwardly toward the enlarged end of the tapered portion and away from the wall thereof to form leg 134. Subsequently, any excess material between legs 132 and 134 may be cut away.

As with grafts 110, 114 and 116, base member 112 also may include a series of radiomarkers for identifying its position during surgical implantation. Thus, one series of radiomarkers 142 may be positioned along the periphery of the proximal end of base member 112, another series of radiomarkers 144 may be positioned along the periphery of the free end of leg 132, and a further series of radiomarkers 146 may be positioned along the periphery of the free end of leg 134. Yet another series of radiomarkers 148 may be arranged around the circumference of leg 134 at its juncture with main body 130. Finally, base member 112 may include a further single radiomarker 150 spaced distally from radiomarkers 142 in alignment with the side of leg 134 opposite leg 132 for indicating to the surgeon the rotational orientation of base member 112.

Preferably, base member 112 is also provided in a range of sizes and geometries. In that regard, the various diameters of base member 112 will most preferably be sized relative to the diameters of grafts 110, 114 and 116 so that the grafts and base member can be joined together with a tight, secure fit. Thus, base members 112 may be provided in which annular sleeve 131 has a diameter in the expanded condition in a range of sizes from about 16 mm to about 25 mm in increments of about 2 mm, with an expanded diameter of about 22 mm being most preferred. Sleeve 131 also may come in a range of lengths from about 2 cm to about 15 cm in increments of about 10 mm. Similarly, leg 132 may have an expanded diameter in a range of sizes from about 10 mm to about 25 mm in increments of about 2 mm, expanded diameters from about 12 mm to about 15 mm being most preferred, and a length in a range of sizes from about 2 cm to about 10 cm in increments of about 10 mm. In a preferred arrangement, leg 134 may be provided with a single diameter at its juncture with main body 130 of basemember 112, rather than with a range of different diameters. In such event, graft 116 would be provided with a corresponding diameter at its proximal end 116a, and may then taper outwardly to the desired diameter at its distal end 116b. Alternatively, leg 134 may be provided in a range of diameters at its juncture with main body 130 to correspond to the diameter of graft 116 where a graft 116 having a uniform diameter within a range of diameters is employed.

As noted above, base member 112 may also be provided with different geometries. That is, the angle at which legs 132 and 134 project from the longitudinal centerline C of main body 130 may be varied to accommodate differences in arterial morphology from one patient to the next. Accordingly, base members 112 may be provided such that leg 132 projects from centerline C at one of a number of different angles α ranging from about 10 degrees to about 60 degrees, in increments of about 5 degrees. Similarly, base members 112 may be provided in which leg 134 projects from centerline C at one of a number of different angles β ranging from about 10 degrees to about 60 degrees, in increments of about 5 degrees. Legs 132 and 134 need not project at the same angle from longitudinal centerline C. In other words, the angles at which legs 132 and 134 project from main body 130 may be determined independently of one another so as to conform as closely as possible to the arterial geometry of the patient. Moreover, the centerlines of legs 132 and 134 need not lie in the same plane as the centerline C of main body 130, but may project from centerline C in a third dimension (outwardly from the page) at one of a number of different angles ranging from about 0 degrees to about 90 degrees, in increments of about 5 degrees. While legs 132 and 134 would typically project at the same angle from centerline C in the third dimension, this need not be the case and base members 112 may be provided in which legs 132 and 134 project at different angles from one another in the third dimension.

Each of grafts 110, 114 and 116 preferably consists of a flexible outer layer 152 which is supported internally along substantially its entire length by an expandable stent 154 which assumes a generally cylindrical or tapered configuration in the expanded condition, depending upon the configuration it is given when initially formed, and which provides the graft with sufficient structural strength to permit the components of modular system 10 to be assembled to one another in situ. In the case of primary graft 110, stent 154 may protrude beyond the proximal end 110a thereof and include one or more barbs 156 for anchoring graft 110 to the wall of aorta 200 to assist in holding modular assembly 100 in place. Alternatively, stent 154 may occupy the exterior of grafts 110, 114 and 116, with the flexible layer 152 extending longitudinally therethrough.

Outer layer 152 is preferably formed from a biocompatible material having sufficient strength to withstand the surgical implantation procedure described more fully below and to withstand the blood flow and other biomechanical forces which will be exerted on modular system 100. Such materials may include, for example, polyester materials, such as DACRON®, polytetrafluoroethylene, expanded polytetrafluoroethylene, polyester materials coated with polytetrafluoroethylene, polyurethane, expanded polyurethane and silicone. Outer layers 152 formed from woven materials are preferred. To reduce the bulk and facilitate the intraluminal delivery of grafts 110, 114 and 116, outer layer 152 preferably has a thickness of about 0.1 mm which is about one-third the thickness of conventional graft materials. It will be appreciated, of course, that the present invention can be practiced using materials which are greater than 0.1 mm in thickness, including conventional graft materials.

Methods for forming tubular woven articles having a uniform diameter are well known in the art and are commonly employed in fabricating conventional grafts. Such methods may be utilized to fabricate the outer layer 152 of grafts 114 and 116. Typical methods make use of a narrow fabric weaving loom where warp threads (i.e., those threads extending in the longitudinal direction of the tube) and weft threads (i.e., those threads extending transverse to the longitudinal direction of the tube) are interlaced with one another. At the weaving station of the loom, the warp threads are fed individually through heddles aligned transverse to the longitudinal direction on one of four or more shafts. The upward and downward movement of the shafts moves a preselected pattern of the warp threads up and then down, two of the shafts moving the warp threads for forming the upper surface of the tube, and two of the shafts moving the warp threads for forming the lower surface of the tube. As the warp threads on one shaft are drawn upwardly and the warp threads on another shaft are drawn downwardly, the weft thread is shuttled in a first direction between those groups of warp threads to weave the upper surface of the tube. The weft thread is then shuttled in a reverse direction between another group of upwardly and downwardly drawn warp threads to weave the lower surface of the tube. The position of the shafts and thus the position of the warp threads is then reversed and the weft thread is again shuttled between the groups of warp threads, the process continuing to weave a tubular shape.

Figure 7:
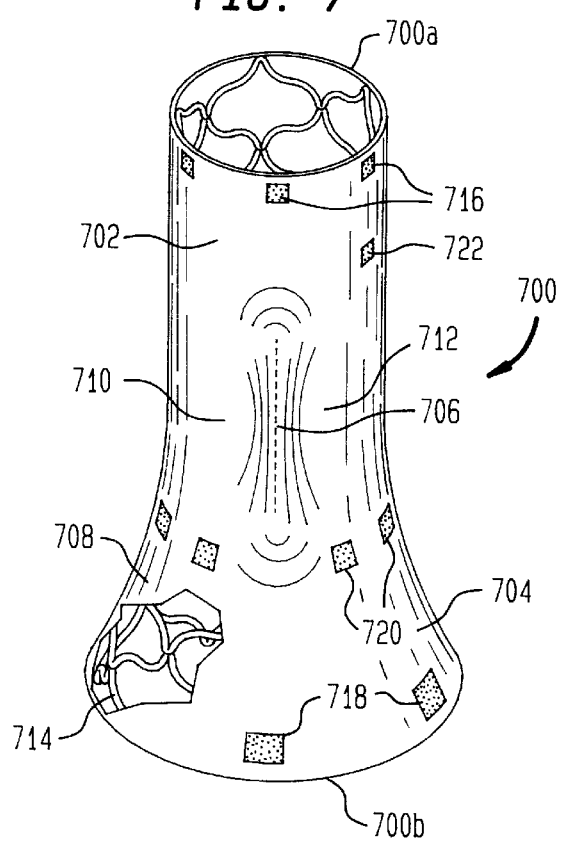
Figure 8:
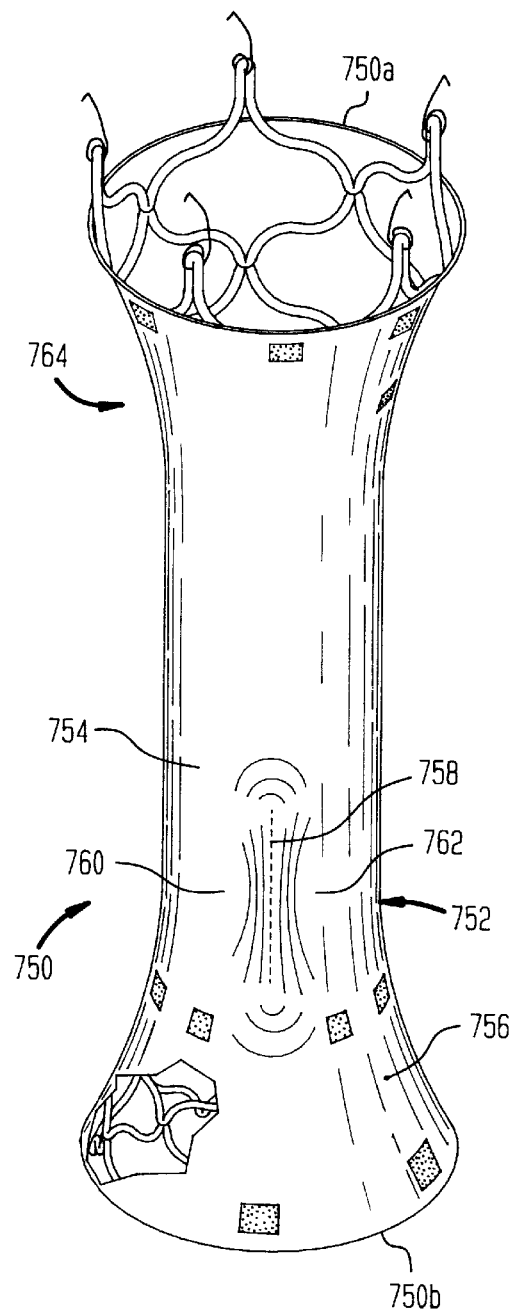
FIG. 8 is a perspective view of a component of a modular system in accordance with yet another embodiment of the present invention.

As they approach the weaving station, the warp threads are fed between the fingers of a front reed which align the threads for weaving and which thus determine the ultimate shape of the woven article. For weaving tubular articles having a substantially constant diameter, such as outer layer 152 of grafts 114 and 116, a conventional front reed which is fixed in place and which has evenly spaced fingers is used to produce constant spacing between the warp threads. Where a tubular article having a gradually increasing or decreasing diameter is desired, however, the conventional reed is replaced with a fan-shaped reed in which the spacing between the fingers is narrow at the bottom and gradually increases toward the top. Such fan-shaped reeds are conventional in the textile industry, and find use for such applications as weaving tapered flat camera straps. In such processes, the reeds are not held in a fixed position, but rather are moved upward or downward to alter the diameter of the article being woven. Thus, when the fan-shaped reed is gradually moved downward as the weaving of the tube advances, the spacing between the warp threads and, hence, the diameter of the tubular article being woven will gradually be increased. Similarly, when the reed is gradually moved upward as the weaving of the tube advances, the spacing between the warp threads will decrease as will the diameter of the tubular article being woven. The rate of movement of the reed will determine the taper of the article being woven; the faster the reed is moved, the larger the angle of taper, and the slower the reed is moved, the smaller the angle of taper. Moving the reed at a constant rate will produce a constant angle of taper. However, changing the rate of movement of the reed enables tubular articles to be formed with curved or changing angles of taper (as shown in FIGS. 7 and 8). The upward or downward movement of the reed, and therefore the degree of taper in the woven article, can be controlled in a known fashion by the use of a stepping motor and a system controller.

As the space between the warp threads is increased to weave a tubular article with an increasing diameter, it is desirable to decrease the spacing between the weft threads so as to maintain the structural integrity of the article being woven. This also can be accomplished in a conventional fashion by employing a solenoid-activated mechanism to withdraw the working pawl in the conventional pawl and ratchet fabric take off system from its normal operating position. Operation of the solenoid can also be dictated by the system controller.

Weaving processes employing a movable fan-shaped reed can be employed to form the outer layer 152 for tapered graft 110. In such process, the front fan-shaped reed of the loom would initially be held in a fixed upper position to weave the substantially uniform diameter tube for annular sleeve 113. When the annular sleeve 113 reaches the desired length, the front reed would be drawn downward at a rate which would produce the desired angle of taper. The front reed would continue to be drawn downward as the weaving process continues until a layer 152 having the desired tubular configuration has been formed.

Stent 154 may be formed from a wire or the like of a low shape-memory material which has been bent back and forth in a curved pattern in the longitudinal direction of the graft and then wrapped in a circumferential direction transverse to the longitudinal direction to form one or more loops of a predetermined circumference. As used herein, the term "low shape-memory material" refers to a material that, once deformed from an initial shape to a subsequent shape, will tend to maintain the subsequent shape and not return to the initial shape. Such materials preferably include biocompatible metals, including, for example, stainless steel, titanium, tantalum, gold, platinum, copper and the like, as well as alloys of these metals. Biocompatible low shape-memory plastics may also be used to form stent 154. Alternatively, stent 154 may be formed from a high shape-memory plastic or alloy, such as nitinol, which automatically transforms from one shape to another shape as its temperature passes through a critical point. Whether stent 154 is formed from a low shape-memory material or from a high shape-memory material is not critical, and impacts on the present invention predominantly in terms of the technique used to intraluminally deliver the components of modular system 100 to the aneurysm site and fix same in place. The structure of preferred stents 154 and methods for forming same are disclosed in commonly assigned U.S. patent application Ser. No. 08/353,066 entitled "High Hoop Strength Intraluminal Stent", the disclosure of which is incorporated by reference herein.

Base member 112 is similar in construction to grafts 110, 114 and 116, and includes a flexible outer layer 160 which is ordinarily formed from the same materials as outer layer 152. An expandable generally Y-shaped stent 162 internally supports outer layer 160 along substantially its entire length, providing structural strength thereto, and is ordinarily formed from the same materials and by the same methods as stent 154. As with grafts 110, 114 and 116, base member 112 may be constructed with stent 162 on the exterior and flexible layer 160 arranged interior thereof.

Grafts 110, 114 and 116 and base member 112 are each radially expandable from a collapsed condition in which the circumferences thereof are minimized so that the components can be delivered to the site of the aortic aneurysm intraluminally, to an expanded condition in which the circumference of each of the components approaches a predetermined maximum circumference. As will be described more fully below, each component is normally held in the collapsed condition by the outer sheath of a catheter during intraluminal delivery. Once properly located, the component is deployed from the catheter and radially expanded until its circumference firmly contacts the interior wall of either the artery in which it is situated or the component to which it is being connected to hold the graft in this implanted location.

Figure 9:
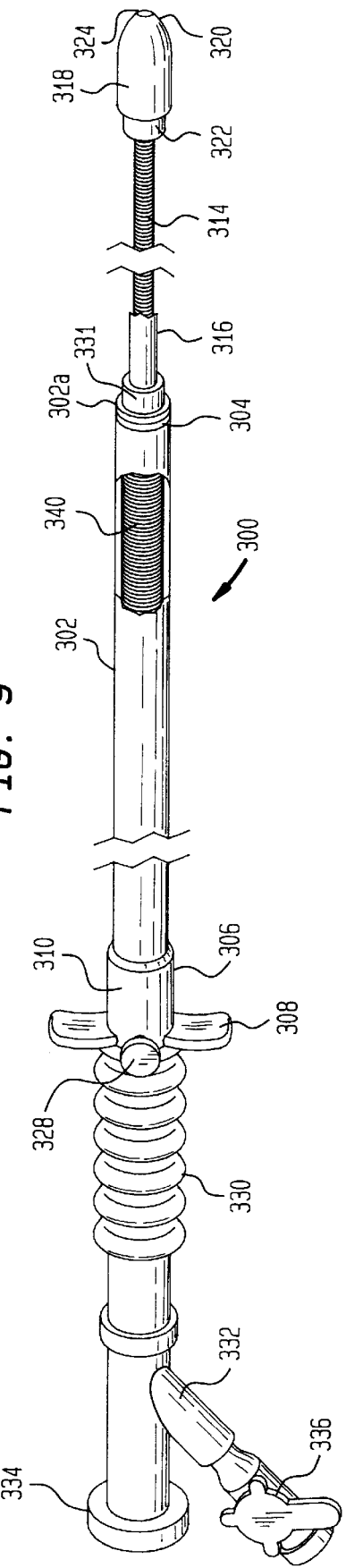
Figure 10:
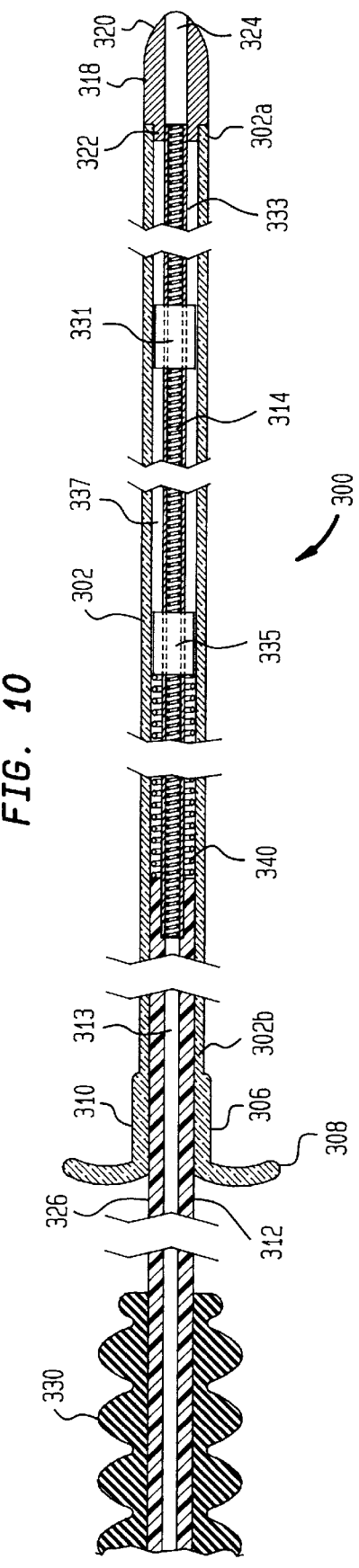
FIG. 10 is a cross-sectional view of the delivery catheter assembly shown in FIG. 9, the sheath thereof being in the fully extended position.

Once the proper sizes for the various components of modular system 100 have been selected, the components are preferably preloaded into one or more disposable delivery catheter assemblies which then may be used by the surgeon to intraluminally introduce the components into the patient and to assemble same to one another in the form of a bifurcated graft. One such delivery catheter assembly 300 is shown in FIGS. 9–10. Delivery catheter assembly 300 includes an elongated tubular outer sheath 302 formed from a conventional polymer which is sufficiently flexible that it will readily bend as catheter assembly 300 is fed through the arterial path during the intraluminal surgical procedure. Typical materials for forming sheath 302 include, for example, nylon, TEFLON polytetrafluoroethylene, polyethylene and the like. The forward end 302a of sheath 302 may include a radiomarker 304 for readily identifying and locating end 302a under fluoroscopy. Radiomarker 304 may take the form of an annular ring formed from a metal, such as stainless steel or platinum-iridium, or a radioopaque polymer, or may consist of any radioopaque material applied to the end 302a of sheath 302. At its rearward end 302b, sheath 302 may include a conventional T-handle 306 having finger grips 308 and a hollow stem 310.

An inner tubular member 312 is arranged in sheath 302 for slidable longitudinal movement with respect thereto. Tubular member 312 defines a continuous internal passageway 313 through delivery catheter 300 so that the delivery catheter can be assembled onto and follow a guidewire during the intraluminal delivery procedure. In that regard, tubular member 312 may be formed from any biocompatible material which resists kinking. In a preferred arrangement, however, tubular member 312 includes a coiled, spring-like wire 314 which is flexible, yet which has sufficient radial strength to resist collapsing due to the forces exerted by the components of modular system 100 when they are loaded in delivery catheter 300. In a highly preferred arrangement, the coil 314 may be surrounded by a thin-walled polymer tube 316 or coated with an impervious polymer layer (not shown) so that medications, dyes and the like may be supplied through passageway 313 to the abdominal aorta repair site.

At one end of coil 314, tubular member 312 includes a tip 318 which may be formed from a biocompatible polymer, such as polyurethane, TEFLON polytetrafluoroethylene, nylon or the like, with a conventional radioopaque marker (not shown) formed or assembled thereon. Tip 318 preferably has an outer diameter which is larger than the inner diameter of sheath 302 so that tip 318 cannot be drawn into sheath 302 as the sheath and tubular member 312 are moved relative to one another. The forward end of tip 318 preferably has a smoothly curved surface 320 to facilitate the forward movement of delivery catheter assembly 300 through the arterial system. At its rearward end, tip 318 may include a reduced diameter portion 322 sized to fit within the sheath 302 so as to axially align tip 318 with sheath 302 in the mated condition and seal the end 302a of the sheath. A bore 324 in tip 318 communicates with the passageway 313 in tubular member 312 to enable a guidewire, medication, dye and the like to exit from delivery catheter assembly 300.

At the opposite end of coil 314, tubular member 312 may include a stabilizer tube 326 which extends outwardly of sheath 302 through the hollow stem 310 of T-handle 306. Stabilizer tube 326 may be formed from any biocompatible material, including polymers such as polyurethane, TEFLON polytetrafluroethylene and nylon, and metals, such as stainless steel. A thumbscrew 328 in T-handle 306 may be actuated to engage stabilizer tube 326, thereby locking tubular member 312 in place with respect to sheath 302. Exterior of sheath 302, stabilizer tube 326 may be fitted with a conventional hand grip 330 and any number of conventional accessories, such as the Y-connector 332, hemostasis valve 334 and stopcock 336 illustrated in FIG. 9.

A cylindrical spacer 331 formed on tubular member 312 at a spaced distance from the rearward end of tip 318 defines a first annular cavity 333 within sheath 302 for holding and delivering the first component of modular system 100 to be deployed during the surgical procedure described below, in this case graft 114. Spacer 331 may also be formed from any biocompatible material, including polyurethane, TEFLON polytetrafluoroethylene, nylon and stainless steel, and preferably includes a radiomarker (not shown) so that its position can be identified by fluoroscopy during the surgical procedure. The length of cavity 333 will depend upon the length of the particular component of modular system 100 to be assembled therein. Thus, cavity 333 preferably will be sufficiently long to accommodate the component, but not so long that there is a substantial unsupported gap between the end of the component and either tip 318 or spacer 331 which may permit sheath 302 to kink as a result of the axial forces applied to feed delivery catheter assembly 300 through the arterial system.

A second spacer 335 having generally the same construction as spacer 331 is formed on tubular member 312 at a spaced distance from the first spacer 331, thus defining a second annular cavity 337 within sheath 302 for holding and delivering the second component of modular system 100 to be deployed during the surgical procedure, in this case base member 112. The length of cavity 337 will be sufficient to accommodate base member 112, but not so long that there is a significant unsupported gap between base member 112 and either spacer 331 or spacer 335.

Delivery catheter assembly 300 further includes a coiled, spring-like wire 340 assembled in sheath 302 between spacer 335 and the end of stabilizer tube 326. Coil 340 radially supports sheath 302 to prevent the kinking of same and provides a structure for transferring the axial load applied through T-handle 306 to spacers 335 and 331, while at the same time not detracting from the overall flexibility of delivery catheter assembly 300.

A method for introducing and assembling the various components of modular system 100 to repair an abdominal aortic aneurysm will now be described with reference to FIGS. 3A–J. The described method assumes that the stents 154 within grafts 110, 114 and 116 and the stent 162 within base member 112 are formed from a memory metal, such that the stents, and hence each of the components, will radially expand automatically as their temperature reaches the transition temperature for the memory metal following deployment within the body. From the method described hereinafter, methods employing balloon expansion techniques for introducing and assembling the components of a modular system 100 in which stents 154 and 162 are formed from low shape-memory materials will be readily apparent to one skilled in the art. Accordingly, a detailed description of such methods is not provided herein.

Figure 3B:
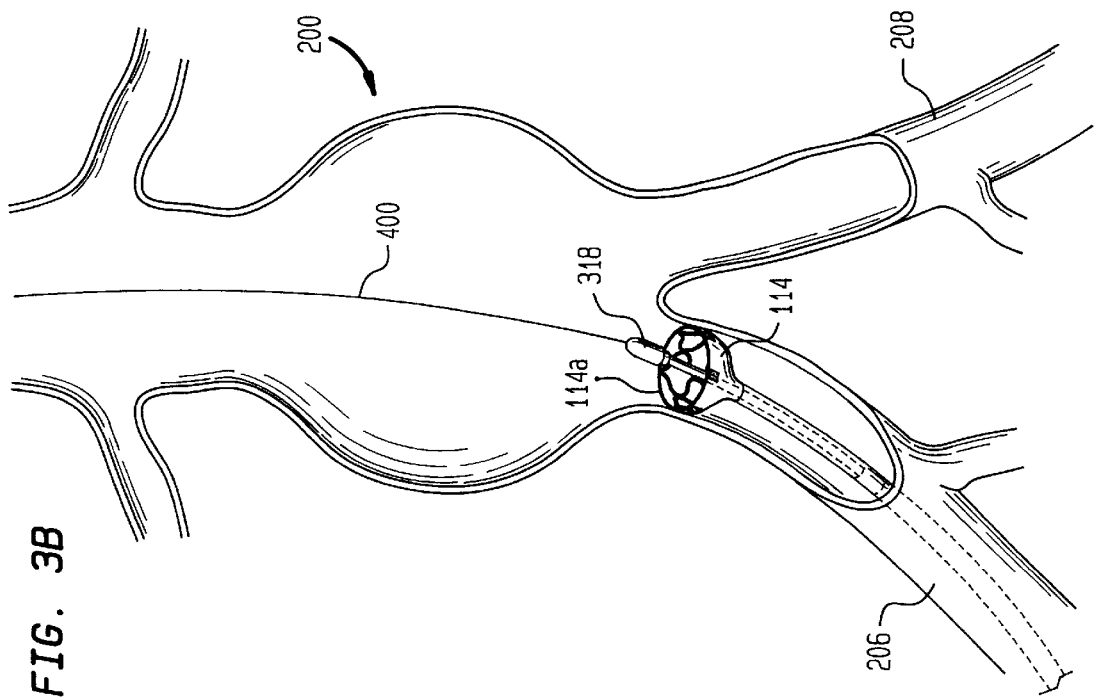
Figure 3A:
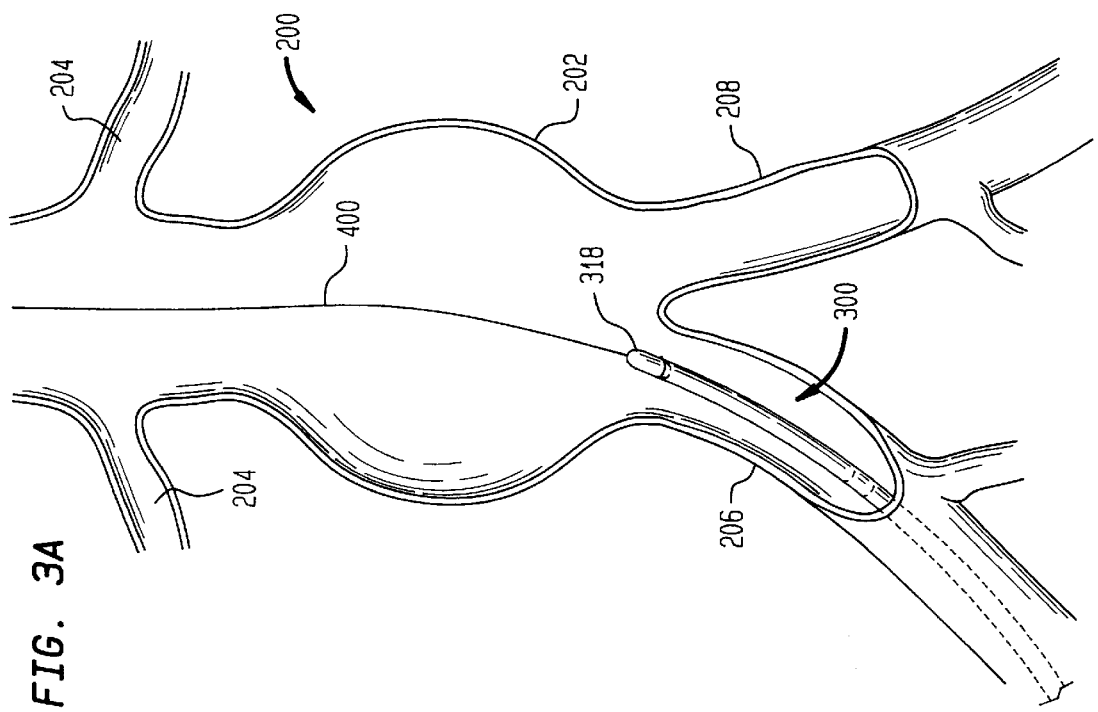

Thus, in a repair method of the present invention, an arteriotomy is initially performed on the right leg and, under conventional fluoroscopic guidance techniques, a first guidewire 400 is introduced through the right femoral artery (not shown) and right iliac 206 into the aorta 200. Delivery catheter assembly 300 containing in succession graft 114 and base member 112 may then be assembled on guidewire 400, the guidewire being threaded through passageway 313 in tubular member 312 and advanced under fluoroscopic guidance until the end 302a of sheath 302 is positioned adjacent the junction of right iliac 206 and aorta 200, as shown in FIG. 3A. At this point, thumbscrew 328 may be loosened and T-handle 306 of delivery catheter assembly 300 pulled backward to partially retract sheath 302 with respect to tubular member 312, thereby exposing the proximal end 114a of graft 114 as illustrated in FIG. 3B. Sheath 302 may then be retracted further to the position illustrated in FIG. 3C wherein the end 302a thereof is aligned with spacer 331, at which point the first annular cavity 333 will be completely open and the entirety of graft 114 will be exposed. With sheath 302 no longer insulating graft 114 and retaining it in the collapsed condition, graft 114 will expand radially as its temperature increases through the transition temperature of the memory metal forming the stent 154 therein. This radial expansion will continue until the outer layer 152 of graft 114 firmly engages the interior wall of iliac 206 to hold graft 114 in this implanted location.

Figure 3F:
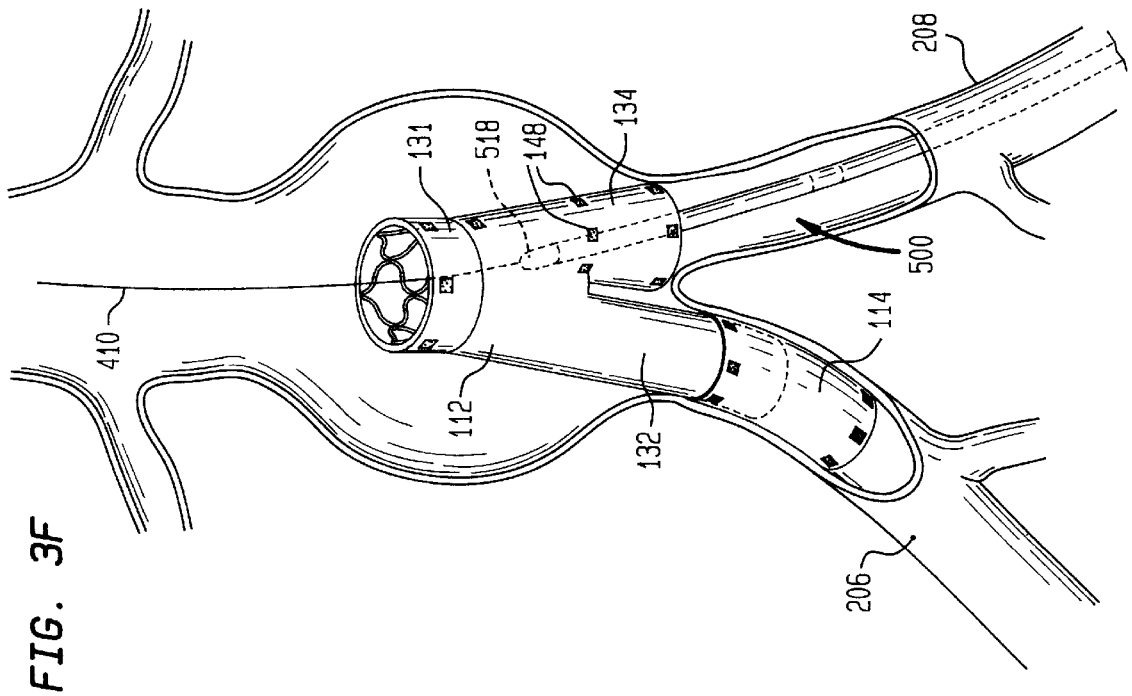
Figure 3E:
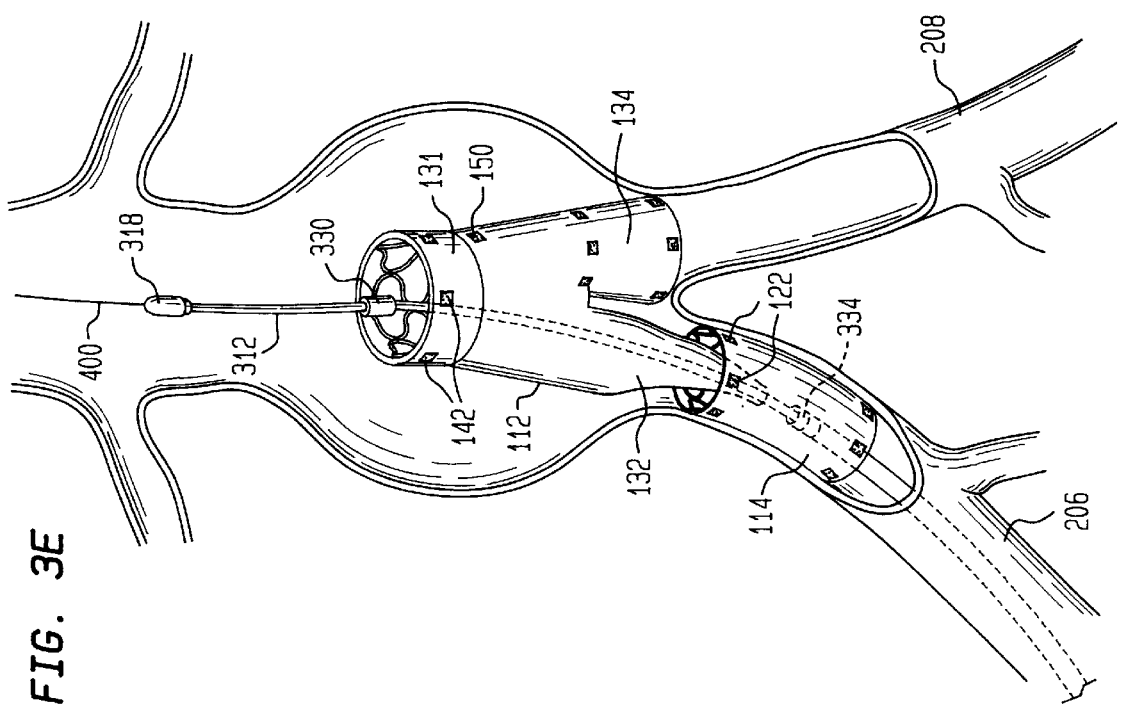
Figure 3G:
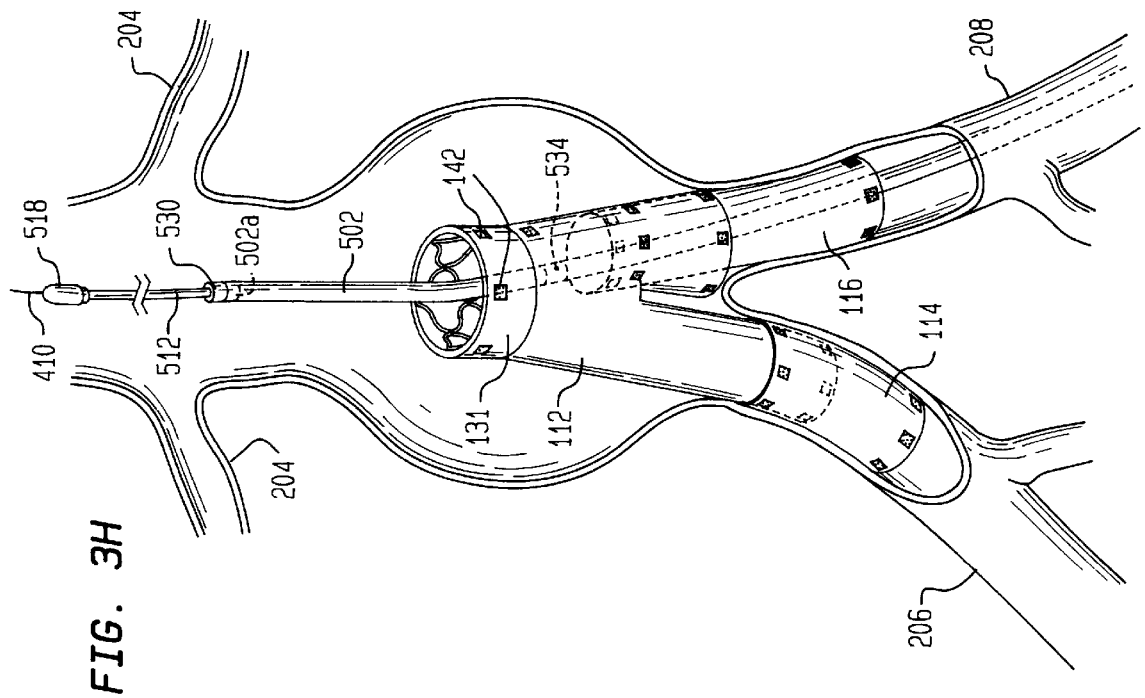

Following deployment of graft 114, thumbscrew 328 may be tightened to lock sheath 302 relative to tubular member 312 and delivery catheter assembly 300 may be advanced as a unit into the base of aneurysm 202, as shown in FIG. 3D, until the radiomarkers 144 on leg 132 of base member 112 are aligned within the proximal end 114a of graft 114, at a spaced distance below the radiomarkers 122. This distance should be such as to provide a sufficient overlap between the proximal end 114a of graft 114 and the free end of leg 132 that a secure connection will be formed between these members. Once properly positioned, thumbscrew 328 may be loosened and the outer sheath 302 of delivery catheter assembly 300 retracted relative to tubular member 312 to expose sleeve 131 on the proximal end of base member 112. At this point, the surgeon may look for the single radiomarker 150 just inwardly of radiomarkers 142 to assure that leg 134 of base member 112 is in alignment with left iliac 208. If leg 134 is not properly aligned, delivery catheter assembly 300 may be rotated until such alignment is achieved. With base member 112 properly positioned, sheath 302 may be retracted further as shown in FIG. 3E until the end 302a thereof is aligned with spacer 335, whereupon the second annular cavity 337 will be completely open and the entirety of base member 112 will be exposed. Again, without sheath 302 retaining it in the collapsed condition, base member 112 will expand radially until the free end of leg 132 contacts and firmly engages the interior wall on the proximal end 114a of graft 114 in overlapping relationship. Forming leg 132 of base member 112 with a diameter in the fully expanded condition which is larger than the fully expanded diameter of graft 114 will assure that the foregoing assembly procedure securely locks base member 112 and graft 114 together and forms a seal which prevents the leakage of blood from therebetween.

Figure 3H:
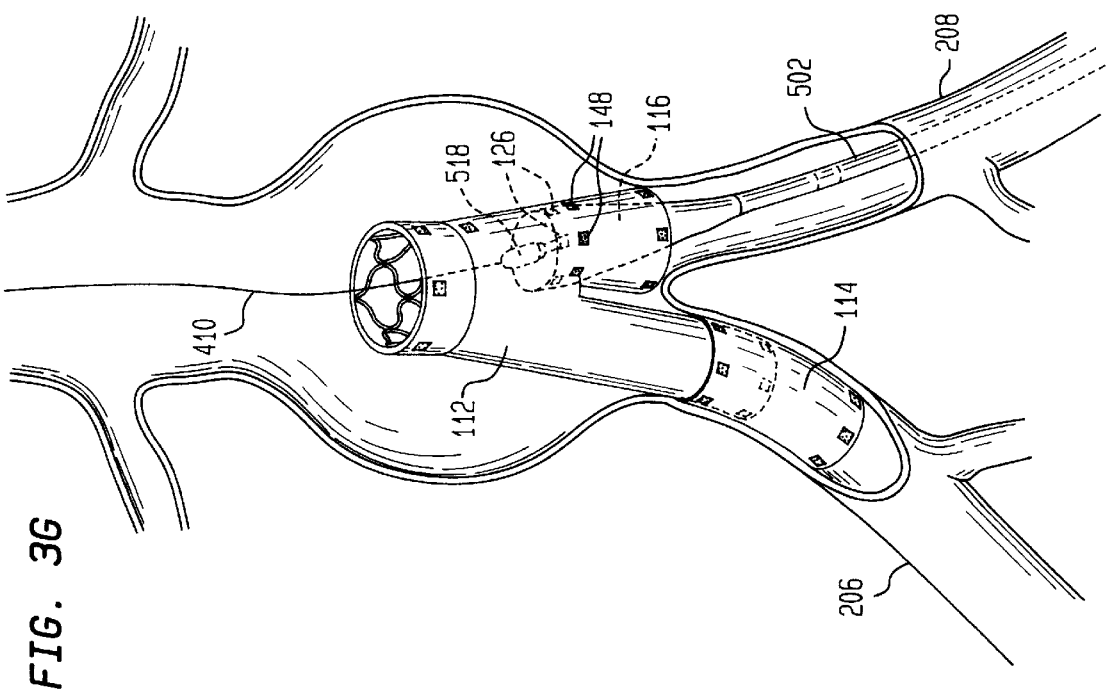

With graft 114 and base member 112 deployed and assembled together, tubular member 312 may be retracted with respect to sheath 302 until the reduced portion 322 of tip 318 is positioned within the end 302a of sheath 302. Thumbscrew 328 may then be tightened to lock these two elements together and the entire delivery catheter assembly 300 may be withdrawn from the patient, with guidewire 400 being retracted into right iliac 206 and temporarily left in place therein. A second arteriotomy may then be performed on the left leg of the patient and, again under fluoroscopic guidance, a second guidewire 410 may be introduced up through the left femoral artery (not shown), through the left iliac 208, into base member 112 through the outlet 140 defined at the free end of leg 134, and finally out through the inlet 136 defined at the free end of sleeve 131. With guidewire 410 in place, guidewire 400 may be fully withdrawn from the patient. A second delivery catheter assembly 500 containing in succession grafts 116 and 110 may then be advanced over guidewire 410 through the left femoral artery and left iliac 208 until the tip 518 thereof is positioned within leg 134 of base member 112, with radiomarkers 126 on the proximal end 116a of graft 116 located a spaced distance above radiomarkers 148 on base member 112 at the juncture of leg 134 and main body 130, all as illustrated in FIG. 3F. When delivery catheter assembly 500 has been properly positioned, the thumbscrew thereon (not shown) may be loosened and sheath 502 partially retracted with respect to tubular member 512, thereby exposing the proximal end 116a of graft 116. With sheath 502 no longer holding the proximal end 116a of graft 116 in the collapsed condition, the proximal end will begin to expand radially until it contacts and firmly engages the inner wall of base member 112 at the juncture between main body 130 and leg 134. Again, a secure leakproof assembly of graft 116 to base member 112 can be obtained by assuring that the diameter of graft 116 in the fully expanded condition is greater than the diameter of base member 112 at the juncture between main body 130 and leg 134, and that a sufficient portion of the proximal end 116a of graft 116 is located above this juncture. The remainder of graft 116 may then be deployed as shown in FIG. 3H by retracting sheath 502 further until the end 502a thereof is aligned with spacer 530.

Figure 3I:
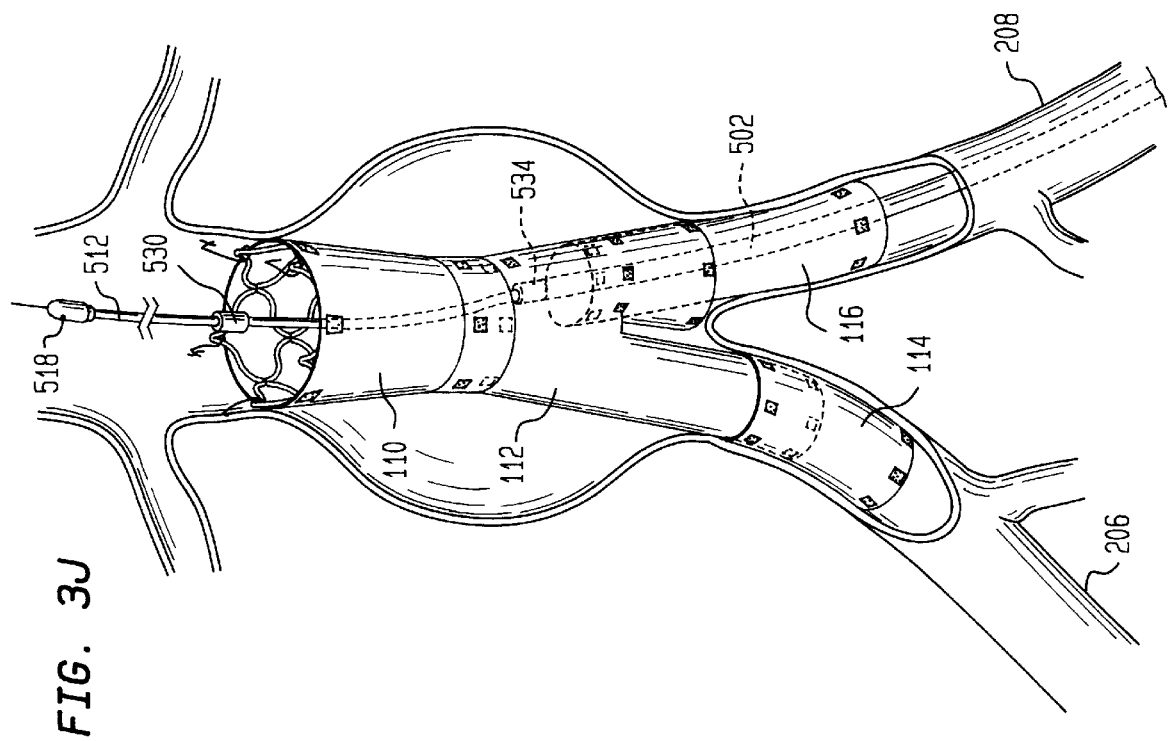
Figure 3J:
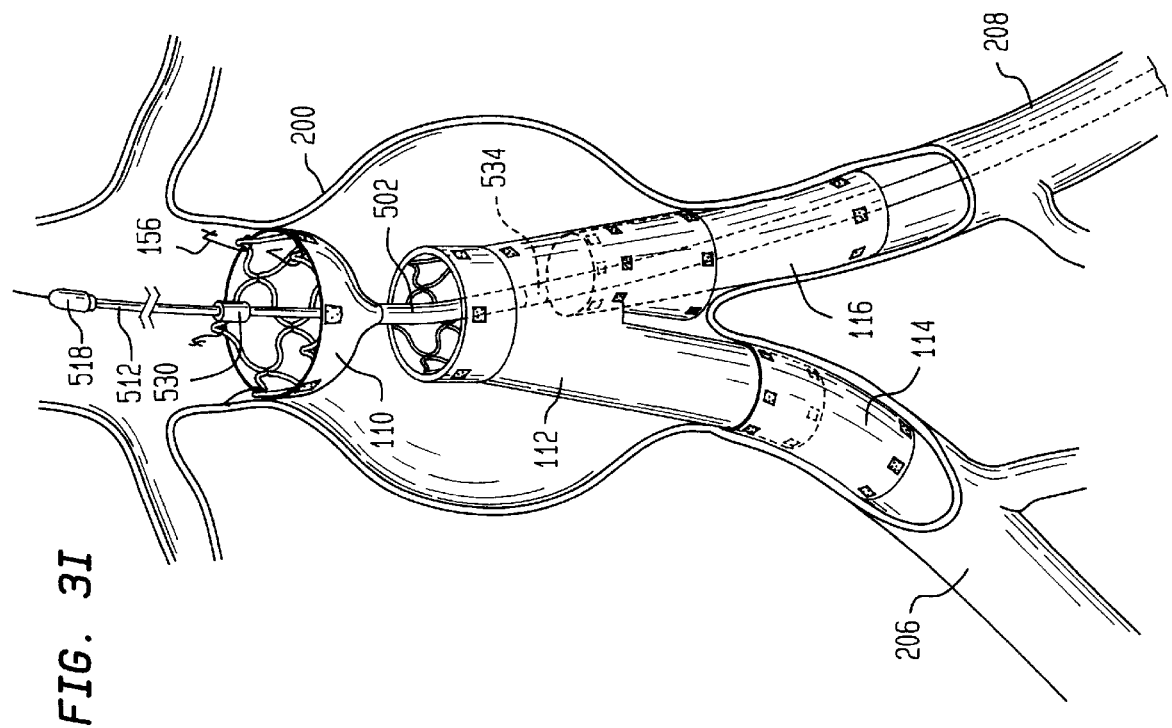

Once graft 116 has been deployed, guidewire 410 may be advanced until the end thereof is positioned above the renal arteries 204. The thumbscrew on delivery catheter assembly 500 may be tightened to lock sheath 502 relative to tubular member 512 and the delivery catheter assembly may then be advanced over guidewire 410 to the position shown in FIG. 3H, wherein the radiomarkers 120 on the distal end 110b of graft 110 are positioned within sleeve 131 of base member 112, but at a spaced distance below radiomarkers 142. When primary graft 110 has been properly located with respect to base member 112, i.e., with a sufficient overlap between the distal end 110b of graft 110 and the proximal end of base member 112, the thumbscrew on delivery catheter assembly 500 may be loosened and sheath 502 retracted relative to tubular member 512 to expose the proximal end 110a of graft 110. As illustrated in FIG. 3I, with sheath 502 no longer holding it in the collapsed condition, the proximal end 110a of graft 110 will expand radially until the outer layer thereof firmly engages the interior wall of aorta 200. This radial expansion will also cause the barbs 156 on the proximal end of graft 110 to contact the inner wall of aorta 200. Tightening the thumbscrew thereof and then tugging slightly on delivery catheter assembly 500 will assure that barbs 156 grab into the inner wall of aorta 200 to assist in holding primary graft 110 and, hence, the proximal end of modular system 100 in place. With barbs 156 securely engaged, the thumbscrew may be loosened and sheath 502 retracted relative to tubular member 512 until the tip 502a of the sheath is aligned with spacer 534 to expose and deploy the remainder of primary graft 110. As primary graft 110 is fully deployed, the distal end 110b thereof will expand radially until it firmly engages the interior wall of sleeve 131, securely locking primary graft 110 to base member 112 in a leakproof arrangement. Tubular member 512 may then be retracted relative to sheath 502 until the reduced diameter portion 522 of its tip 518 is positioned within the end 502a of the sheath. Tubular member 512 may then be locked to sheath 502 by tightening the thumbscrew of delivery catheter assembly 500, and the entire assembly may be withdrawn from the patient. Subsequently, guidewire 410 may be withdrawn from the patient and the arteriotomies sutured.

Once deployed and assembled-together according to the foregoing procedure, the components of modular system 100 form..a. bifurcated graft which is fully self supporting. That is, as a result of its bottom-up assembly, the biomechanical forces exerted on the graft, particularly from the flow of blood, are supported along its entire length in a columnar fashion.

It will be appreciated, of course, that variations in the foregoing procedure can be made without departing from the scope of the present invention. For example, delivery catheter assembly 300 may be fabricated with three spacers defining three annular cavities in succession, with graft 114 loaded in the first annular cavity, base member 112 loaded in the second annular cavity and primary graft 110 loaded in the third annular cavity. In such event, graft 114 and base member 112 may be deployed in succession as described above, following which the delivery catheter assembly may be advanced to deploy primary graft 110. Subsequently, graft 116 would be deployed and assembled to base member 112 as described above utilizing a second delivery catheter assembly having only one spacer defining a single annular cavity for holding graft 116.

Other variations from the foregoing method are also possible. In this regard, rather than relying merely upon the outward radial forces exerted by the expanding stent structures of grafts 110 and 116 and base member 112 to securely lock the components together, the appropriate ends of these components may be provided with mechanical structures, such as barbs, sutures and the like, to assure that the components are securely held together.

Figure 4:
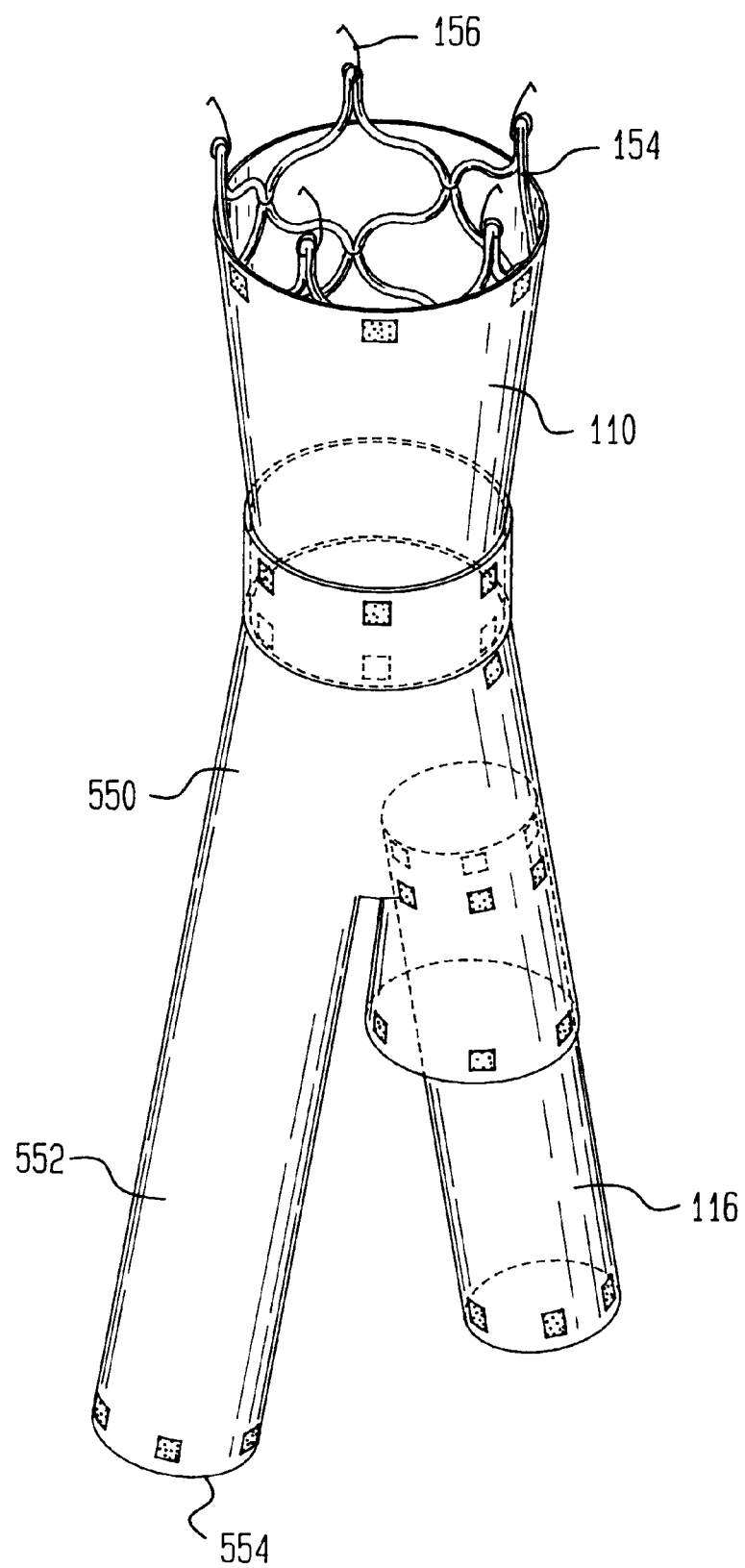
FIG. 4 is a perspective assembled view of a modular system in accordance with an alternate embodiment of the present invention.

By changing the configuration of the various components of the modular system, still other variations in the surgical procedure are possible. Thus, referring to FIG. 4, the modular system may include a base member 550 having an integral elongated leg 552. Leg 552 would typically be formed with a substantially uniform diameter and a sufficient length that at least the distal end 554 thereof will securely engage right iliac 206 upon.. the deployment of base member 550, thereby eliminating the need to deploy a separate graft in right iliac 206 and connect the base member thereto, as in the case with graft 114 and base member 112 described above. As a result, the use of base member 550 results in a simpler surgical procedure while maintaining substantially all of the advantages associated with the modular system 100 of the present invention.

Figure 5:
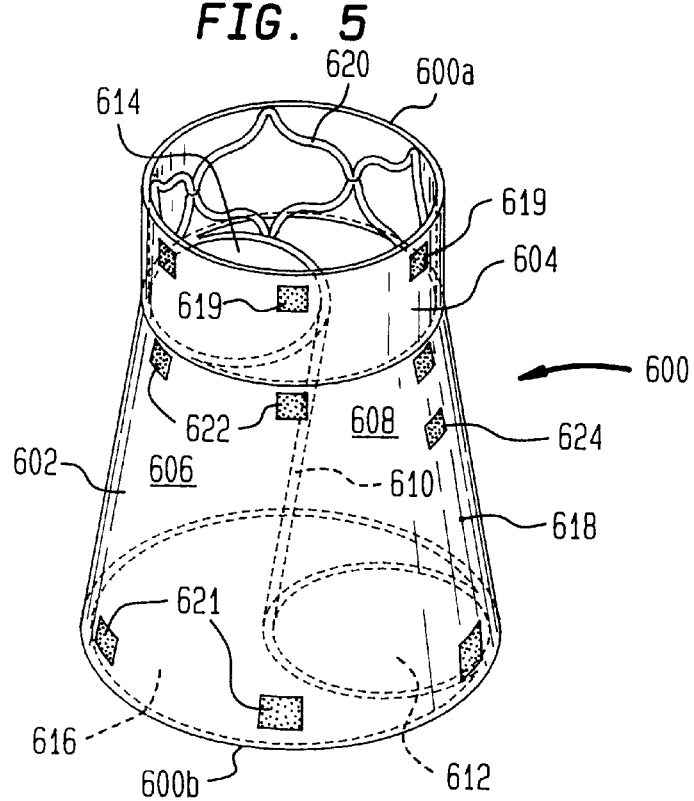
FIGS. 5, 6 and 7 are perspective views of base members for use in connection with modular systems in accordance with still further embodiments of the present invention.

Furthermore, the base member need not have integrally formed legs depending distally therefrom. For example, in accordance with another embodiment of the present invention, the modular system may include a base member 600 such as shown in FIG. 5. Base member 600 has a generally frustoconical main body 602 which gradually decreases in diameter from the distal end 600b of the base member to its juncture with an annular sleeve 604. Sleeve 604 has a substantially uniform diameter until its terminus at the proximal end 600a of base member 600. The main body 602 of base member 600 is divided into two portions 606 and 608 by a web 610 which extends from the distal end 600b of the base member to the juncture between main body 602 and sleeve 604. Web 610 is connected within base member 600, such as by sewing, heat welding or the like, so as to define a substantially circular opening 612 on one side of the distal end 600b of base member 600, and another substantially circular opening 614 on the other side of base member 600 at the juncture between main body 602 and annular sleeve 604. The diameter of opening 612 is preferably large enough to readily accept the proximal end 116a of graft 116, but not so large as to interfere with the insertion of the proximal end 114a of graft 114 into the remaining crescent-shaped opening 616 at the distal end 600b of base member 600. Hence, the diameter of opening 612 is preferably between about one half and three quarters of the diameter of base member 600 at its distal end. As for opening 614, it preferably has a diameter which is smaller than the fully expanded diameter of graft 114 at its proximal end 114a.

As with the components of modular system 100 described above, base member 600 preferably consists of a flexible outer layer 618 which is supported internally along substantially its entire length by an expandable stent 620. In a preferred arrangement, web 610 is connected within base member 600 after stent 620 has been placed within outer layer 618.

Base member 600 may also be provided with a plurality of radiomarkers for locating the various regions thereof under fluoroscopy. Thus, base member 600 may include one series of radiomarkers 619 around the periphery of proximal end 600a, another series of radiomarkers 621 around the periphery of distal end 600b, and another series of radiomarkers 622 formed around the periphery of base member 600 at the juncture between main body 602 and annular sleeve 604. A further single radiomarker 624 may be positioned distally of radiomarkers 622 in alignment with the side of base member 600 opposite opening 614 for indicating the rotational orientation of the base member.

The procedure for implanting and assembling a modular system incorporating base member 600 is different from that described above where the modular system utilizes base member 112. More particularly, rather than deploying and assembling the components from the bottom up as described above, when a base member 600 is utilized the components are deployed and assembled from the top down. That is, the primary graft 110 would be the first component deployed followed by base member 600. In this procedure, however, rather than inserting and expanding the distal end 110b of primary graft 110 within the proximal end of the base member to join these components together, just the opposite procedure is performed. In other words, once primary graft 110 has been deployed, base member 600 would be deployed so that its proximal end 600a is inserted into and expands within the distal end 110b of primary graft 110. Subsequently, graft 116 may be fed upwardly until its proximal end 116a enters base member 600 through opening 612. With the proximal end 116a of graft 116 positioned at a spaced distance above opening 612 (as determined by radiomarkers appropriately placed on the components), graft 116 may be deployed whereupon it will become securely locked within portion 608 of base member 600, with the substantially circular periphery of graft 116 sealing against the substantially circular periphery of opening 612 to prevent the leakage of blood therebetween. As it radially expands, the distal end 116b of graft 116 will engage and become secured within left iliac 208. Graft 110, base member 600 and graft 116 may be deployed in succession from a single delivery catheter assembly similar in construction to delivery catheter assembly 300, yet having a series of three annular cavities. A second delivery catheter assembly may be fed through crescent-shaped opening 616 in base member 600 and then upwardly therefrom to position the proximal end 114a of graft 114 at a spaced distance above opening 614 (also as determined by appropriately placed radiomarkers). Upon deployment of graft 114 in this position, the substantially circular periphery thereof will firmly engage the substantially circular periphery of opening 614 to similarly seal against the leakage of blood from therebetween. The distal end 114b of graft 114, as it radially expands, will engage and become secured within right iliac 206.

Figure 6:
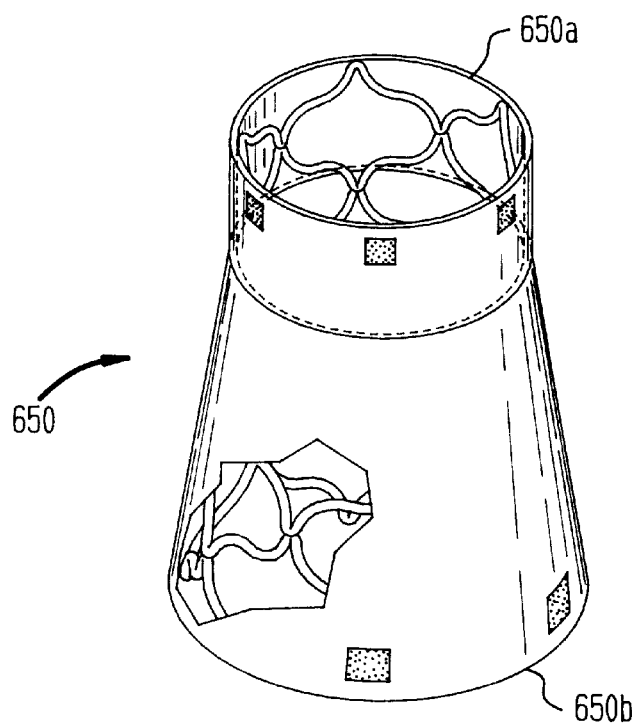

In a variant of the foregoing embodiment, the base member may be formed with the general shape of base member 600, but without the internal web 610. A base member 650 in accordance with this embodiment is illustrated in FIG. 6. Base member 650 is intended to be used in those situations in which the modular system is to be assembled with no iliac grafts 114 and 116. Thus, the modular system would include primary graft 110 and base member 650 which may be deployed either as described immediately above in connection with base member 600 (i.e., primary graft 110 first followed by base member 650), or as described previously in connection with base member 112 (i.e., base member 650 first followed by primary graft 110). However, in positioning base member 650, the surgeon would ensure not only that the proximal end 650a of base member 650 will overlap with the distal end 110b, of graft 110, but also that the distal end 650b of base member 650 will lie against the apex between iliacs 206 and 208, whereby the arterial wall at the apex may support the modular system in its fully deployed and assembled condition. In this scenario, blood flow into graft 110 and through base member 650 will divide at the apex as it exits from the distal end 650b of the base member and will flow into both the right iliac 206 and left iliac 208.

A still further embodiment of a base member 700 in accordance with the present invention is shown in FIG. 7. In one region 702 extending from proximal end 700a along a major portion of its length, base member 700 has a substantially uniform diameter. The diameter of base member 700 then gradually increases in a second region 704 thereof until its terminus at distal end 700b. Tapered region 704 may be formed by the same methods used to form the taper of primary graft 110, as discussed more fully above.

Base member 700 further includes a stitch line 706 which extends in the longitudinal direction thereof within region 702, the stitch line joining the outer layer 708 on the diametrically opposed surfaces of base member 700 to define two tubular channels 710 and 712 intermediate proximal end 700*a* and distal end 700*b*. As with the other components of the modular systems described above, the outer layer 708 of base member 700 is supported internally along substantially its entire length by an expandable stent 714. In that regard, stent 714 may consist of an assembly of several members which independently support tapered region 704, tubular channels 710 and 712, and the proximal end of base member 700. Base member 700 may also be provided with radiomarkers, including one series of radiomarkers 716 formed around the periphery of proximal end 700*a*, another series of radiomarkers 718 formed around the periphery of distal end 700*b*, and another series of radiomarkers 720 formed around the periphery of the base member at the distal end of stitch line 706. In addition, base member 700 may include a further single radiomarker 722 spaced distally of radiomarkers 716 in alignment with the side of tubular channel 712 opposite tubular channel 710 for indicating the rotational orientation of the base member.

In a variant of this embodiment, tubular channels 710 and 712 may consist of tubes of substantially uniform diameter which are independent of one another. Such embodiment would look similar to base member 700 as illustrated in FIG. 7, but would have an elongated through hole in place of stitch line 706. Such embodiment may be formed, for example, from two devices having a tapered region (as at 704) and two tubular legs extending from the tapered region, one device being inverted relative to the other and the devices being joined to one another at their tubular legs.

One procedure for implanting and assembling a modular system incorporating base member 700 may be similar to that described above in connection with base member 600. That is, the primary graft 110 would be deployed first, following which base member 700 may be deployed with its proximal end 700*a* inserted into and expanded within the distal end 110*b* of primary graft 110. Graft 114 may then be fed upwardly until its proximal end 114*a* resides within tubular channel 710 at a spaced distance above radiomarkers 720. Upon its deployment, the proximal end 114*a* of graft 114 will become securely locked within tubular channel 710 and the distal end 114*b* thereof will engage and become secured within right iliac 206. Graft 116 may then be fed upwardly until its proximal end 116*a* lies within tubular channel 712 at a spaced distance above radiomarkers 720. Upon deployment of graft 116, the proximal end 116*a* thereof will become securely locked within tubular channel 712 and the distal end 116*b* thereof will engage and become secured within left iliac 208. It will be appreciated from the foregoing that graft 110, base member 700 and graft 114 may be deployed in succession from a first delivery catheter assembly, with graft 116 being deployed from a second delivery catheter assembly. In an alternate procedure employing base member 700, the base member may be deployed first, followed in succession by grafts 110, 114 and 116.

In a variant of the foregoing embodiment, base member 700 and graft 110 may be combined as a single component 750, illustrated in FIG. 8. Component 750 thus may include a bottom portion 752 which has substantially the same structure as base member 700 described above, including a region 754 having a substantially uniform diameter, a region 756 which gradually increases in diameter as it approaches the distal end 750*b* of component 750, and a stitch line 758 which defines two tubular channels 760 and 762 within component 750. At its upper end, component 750 includes an integrally formed region 764 which begins with a substantially uniform diameter and which gradually increases in diameter as it approaches the proximal end 750*a* thereof.

Forming portions 752 and 764 as a single integral unit thus eliminates the need to deploy a separate graft 110 within aorta 200 and connect the base member thereto. As a result, modular systems incorporating component 750 provide all of the advantages of the present invention while allowing for a simpler surgical procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A modular prosthesis for repairing an aortic aneurysm, comprising a base member foldable radially between a collapsed configuration and an expanded configuration and extending longitudinally between a proximal end and a distal end, said base member having a single inlet at said proximal end and dividing means for forming first and second passageways communicating between said proximal and distal ends, a primary tubular limb foldable radially between a collapsed configuration and an expanded configuration and having a proximal end and a distal end, said primary limb having a single inlet at said proximal end and a single outlet at said distal end, said primary limb being formed separately from said base member and being adapted to lie in the aorta with said proximal end pointing toward the heart, and joining means for intraluminally joining said distal end of said primary limb to said proximal end of said base member.

2. The modular prosthesis as claimed in claim 1, further comprising a secondary tubular limb foldable radially between a collapsed configuration and an expanded configuration and having a proximal end and a distal end, and connecting means for connecting said proximal end of said secondary limb to said distal end of said base member.

3. The modular prosthesis as claimed in claim 2, further comprising another secondary tubular limb foldable radially between a collapsed configuration and an expanded configuration and having a proximal end and a distal end, and attaching means for attaching said proximal end of said another secondary limb to said distal end of said base member.

4. A modular prosthesis for repairing a tubular anatomical structure, comprising a base member foldable radially between a collapsed configuration and an expanded configuration and having a proximal end and a distal end, said base member including a main leg on said proximal end thereof and first and second legs on said distal end thereof, said main leg extending in an axial direction and having a main passageway extending longitudinally therein and defining an inlet on a free end thereof, said first leg being oriented at a first angle to said axial direction and having a passageway extending longitudinally therein and communicating with said main passageway, said first leg defining a first outlet on a free end thereof, and said second leg being oriented at a second angle to said axial direction and having a passageway extending longitudinally therein and communicating with said main passageway, said second leg defining a second outlet on a free end thereof, a primary tubular limb foldable radially between a collapsed configuration and an expanded configuration and having a proximal end and a distal end, joining means for intraluminally joining said distal end of said primary limb to said proximal end of said base member, at least one secondary tubular limb foldable radially between a collapsed configuration and an expanded configuration and having a proximal end and a distal end, and connecting means for connecting said proximal end of said secondary limb to said distal end of said base member.

5. The modular prosthesis as claimed in claim 4, wherein said base member includes a first distance between said inlet and said first outlet and a second distance between said inlet and said second outlet, said first distance being larger than said second distance.

6. The modular prosthesis as claimed in claim 4, wherein each of said first and second angles are between about 10 degrees and about 60 degrees.

7. The modular prosthesis as claimed in claim 6, wherein said first angle is different than said second angle.

8. The modular prosthesis as claimed in claim 4, wherein said main leg is oriented in a primary plane, and at least one of said first and second legs is oriented in a plane different than said primary plane.

9. The modular prosthesis as claimed in claim 4, wherein said first leg has a substantially uniform diameter of between about 10 mm and about 25 mm in said expanded configuration.

10. The modular prosthesis as claimed in claim 4, wherein said base member includes a crotch defined between said first and second legs, and said first leg has a length between said crotch and said first outlet of between about 2 cm and about 15 cm.

11. The modular prosthesis as claimed in claim 4, wherein said second leg has a diameter which decreases in size from said second outlet toward said main leg.

12. The modular prosthesis as claimed in claim 4, further comprising another secondary tubular limb foldable radially between a collapsed configuration and an expanded configuration and having a proximal end and a distal end, and attaching means for attaching said proximal end of said another secondary limb to said distal end of said base member.

13. A modular prosthesis for repairing a tubular anatomical structure, comprising a base member foldable radially between a collapsed configuration and an expanded configuration and having a proximal end and a distal end, a primary tubular limb foldable radially between a collapsed configuration and an expanded configuration and having a proximal end and a distal end, joining means for intraluminally joining said distal end of said primary limb to said proximal end of said base member, one secondary tubular limb foldable radially between a collapsed configuration and an expanded configuration and having a proximal end and a distal end, connecting means for connecting said proximal end of said one secondary limb to said distal end of said base member, another secondary tubular limb foldable radially between a collapsed configuration and an expanded configuration and having a proximal end and a distal end, and attaching means for attaching said proximal end of said another secondary limb to said distal end of said base member.

14. The modular prosthesis as claimed in claim 13, wherein said another secondary limb has a substantially uniform diameter of between about 10 mm and about 25 mm in said expanded configuration.

15. The modular prosthesis as claimed in claim 13, wherein said another secondary limb has a first diameter at said proximal end and a second diameter at said distal end different than said first diameter.

16. The modular prosthesis as claimed in claim 13, wherein said another secondary limb has a length between said proximal end and said distal end of between about 4 cm and about 15 cm.

17. A modular prosthesis for repairing a tubular anatomical structure, comprising a base member extending longitudinally between a proximal end defining an inlet and a distal end defining first and second outlets, said base member being foldable radially between a collapsed configuration and an expanded configuration, a primary tubular limb having a proximal end and a distal end and being foldable radially between a collapsed configuration and an expanded configuration, said distal end of said primary limb in said expanded configuration being matable in overlapping circumferential engagement with said inlet of said base member when said base member is in said expanded configuration to join said primary limb to said base member, and at least one secondary tubular limb having a proximal end and a distal end and being foldable radially between a collapsed configuration and an expanded configuration, said proximal end of said at least one secondary limb being matable in overlapping circumferential engagement with one of said first and second outlets of said base member when said base member is in said expanded configuration to join said at least one secondary limb to said base member.

18. The modular prosthesis as claimed in claim 17, further comprising another secondary tubular limb having a proximal end and a distal end and being foldable radially between a collapsed configuration and an expanded configuration, said proximal end of said another secondary limb being matable in overlapping circumferential engagement with another of said first and second outlets of said base member when said base member is in said expanded configuration to join said another secondary limb to said base member.

* * * * *